United States Patent
Samuelson et al.

(10) Patent No.: US 8,981,067 B2
(45) Date of Patent: Mar. 17, 2015

(54) COMPOSITION, METHOD AND KIT FOR OBTAINING PURIFIED RECOMBINANT PROTEINS

(75) Inventors: James C. Samuelson, Newburyport, MA (US); Carine Robichon-Iyer, Cambridge, MA (US); Jianying Luo, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 208 days.

(21) Appl. No.: 13/821,113

(22) PCT Filed: Aug. 26, 2011

(86) PCT No.: PCT/US2011/049356
§ 371 (c)(1),
(2), (4) Date: Apr. 24, 2013

(87) PCT Pub. No.: WO2012/033653
PCT Pub. Date: Mar. 15, 2012

(65) Prior Publication Data
US 2015/0037866 A1    Feb. 5, 2015

Related U.S. Application Data

(60) Provisional application No. 61/381,736, filed on Sep. 10, 2010.

(51) Int. Cl.
| | |
|---|---|
| *A61K 38/00* | (2006.01) |
| *C07K 1/22* | (2006.01) |
| *C07K 1/36* | (2006.01) |
| *A61K 39/00* | (2006.01) |
| *C12N 9/00* | (2006.01) |

(52) U.S. Cl.
CPC .............. *C12N 9/93* (2013.01); *C12N 2810/55* (2013.01); *C12Y 601/01007* (2013.01)
USPC ....................................................... 530/412

(58) Field of Classification Search
None
See application file for complete search history.

(56) References Cited

U.S. PATENT DOCUMENTS

| | | |
|---|---|---|
| 5,284,933 A | 2/1994 | Dobeli et al. |
| 5,310,663 A | 5/1994 | Dobeli et al. |
| 7,176,298 B2 | 2/2007 | Tchaga et al. |
| 2006/0030007 A1 | 2/2006 | Byrd et al. |

OTHER PUBLICATIONS

Bolanos-Garcia et al Biochim Biophys Acta 1760 1304-1313 2006.
Kimple M.E. and Sondek J. Current Protocols in Protein Science Unit 91-19 2004.
Finzi et al J Virological Methods 111 69-73 2003.
Gaberc-Porekar et al J Biochem Biophys Methods 49 335-360 2001.
Hamilton et al J Bacteriology 4617-4622 1989.
Lichty et al Protein Exp Purif 41 91-105 2005.
Lochkamp et al J Struct Biol 155 111-113 2006.
Mateo et al J Chromatography A 915 97-106 2001.
Parsy et al J Chromatography B 853 314-319 2007.
Tagwerker et al Mol Cell Proteomics 5 737-748 2006.
Muller et al Analytical Biochemistry 259 54-61 1998.
Chong et al Gene 192 271-281 1997.
Arnold, F.H. Biotechnology, 9(2):151-156 1991.
Sulkowski, E. Bioessays, 10(5):170-175 1989.
Graslund, et al., Nature Methods, 5:135-146 2008.
Cronan, J. Biol. Chem., 265:10327-10333 1990.
Beckett, et al., Protein Science, 8:921-929 1999.
Freuler, et al., Protein Expression and Purification, 59:232-241 2008.
Yin, et al., PNAS 102:15815-15820 2005.
Zhou, et al., ACS Chem. Biol., 2:337-346 2007.
Swingle, et al., Mol Microbiol., 75:138-148 2010.
Robichon, et al., Applied and Environmental Microbiology, 77: 4634-4646 2011.
Aslanidis, et al., Nucleic Acids Reasearch, 18: 6069-6074 1990.
Haun, et al., Biotechniques, 13:515-518 1992.
Bitinaite, et al, Nucleic Acids Research, 35(6): 1992-2002 2007.
Chen, et al., J. Biol. Chem., 278:23295-23300 2003.
McCluskey, et al., Protein Science, 16(12): 2726-2732 2007.
Tiwari, et al., Protein Expression and Purification, 70(2): 191-195 2010.
International Application No. PCT/US2011/049356, International Search Report, Dec. 7, 2011.

*Primary Examiner* — Suzanne M Noakes
*Assistant Examiner* — Gerard Lacourciere
(74) *Attorney, Agent, or Firm* — New England Biolabs, Inc; Harriet M. Strimpel

(57) ABSTRACT

Compositions relating to a combination of two types of separation matrix; and to variant host cells which contain at least one essential host protein that is fused to an affinity binding tag or has been mutated to replace at least two of a plurality of histidines or basic amino acids are provided. Methods are also provided that relate to isolating a recombinant protein from a lysate.

12 Claims, 20 Drawing Sheets

FIG. 2-1 pMAKCBD allele exchange vector (SEQ ID NO:49)

```
GACGCTCTCCCTTATGCGACTCCTGCATTAGGAAGCAGCCCAGTAGTAGGT
TGAGGCCGTTGAGCACCGCCGCCGCAAGGAATGGTGCCAATACGCAAACCG
CCTCTCCCCGCGCGTTGGCCGATTCATTAATGCAGCTGGCACGACAGGTTT
CCCGACTGGAAAGCGGGCAGTGAGCGCAACGCAATTAATGTGAGTTAGCTC
ACTCATTAGGCACCCCAGGCTTTACACTTTATGCTTCCGGCTCGTATGTTG
TGTGGAATTGTGAGCGGATAACAATTTCACACAGGAAACAGCTATGACCAT
GATTACGCCAAGCTTGCATGCCTGCAGGCTTCGAGCTCGAACAACAACAAC
AATAACAATAACAACAACCTCCAGTCGACGACAAATCCTGGTGTATCCGCT
TGGCAGGTCAACACAGCTTATACTGCGGGACAATTGGTCACATATAACGGC
AAGACGTATAAATGTTTGCAGCCCCACACCTCCTTGGCAGGATGGGAACCA
TCCAACGTTCTGCCTTGTGGCAGCTTCAATAAGCGATCGCTGAACATGCC
TTTTTTCGTAAGTAAGCAACATAAGCTGTCACGTTTTGTGATGGCTATTAG
AAATTCCTATGCAACAACTGAAAAAAATTACAAAAAGTGCTTTCTGAACT
GAACAAAAAGAGTAAAGTTAGTCGCGTAGGGTACAGAGGTAAGATGTTCT
ATCTTTCAGACCTTTTACTTCACGTAATCGGATTTGGCTGAATATTTTAGC
CGCCCCAGTCAGTAATGACTGGGGCGTTTTTTATTGGGCGAAAGAAAAGAT
CCGTAATGCCTGATGCGCTATGTTTATCAGGCCAACGGTAGAATTGTAATC
TATTGAATTTACGGGCCGGATACGCCACATCCGGCACAAGCATTAAGGCAA
GAAAATTATTCGCCGTCCTGCGTTTCTTCTACAGGCTGCATCTCGCTAAAC
CAGGTATCCAGTTTCTGCCGCAGCTTGTCCACGCCTTGTTTCTTCAACGAA
GAAAACGTTTCAACCTGCACATCACCGTTAAACGCCAGTACAGCTTCACGC
ACCATATTCAATTGCGCTTTACGTGCGCCGCTTGCCAGTTTGTCCGCTTTG
GTCAGCAGCACCAGAACGGCGATATTGCTGGGTACCGAGCTCGAATTCACT
GGCCGTCGTTTTACAACGTCGTGACTGGGAAAACCCTGGCGTTACCCAACT
TAATCGCCTTGCAGCACATCCCCCTTTCGCCAGCTGGCGTAATAGCGAAGA
GGCCCGCACCGATCGCCCTTCCCAACAGTTGCGCAGCCTGAATGGCGAATG
AGCTTATCGATGATAAGCTGTCAAACATGGCCTGTCGCTTGCGGTATTCGG
AATCTTGCACGCCCTCGCTCAAGCCTTCGTCACTGGTCCCGCCACCAAACG
TTTCGGCGAGAAGCAGGCCATTATCGCCGGCATGGCGGCCGACGCGCTGGG
CTACGTCTTGCTGGCGTTCGCGACGCGAGGCTGGATGGCCTTCCCCATTAT
```

FIG. 2-2

```
GATTCTTCTCGCTTCCGGCGGCATCGGGATGCCCGCGTTGCAGGCCATGCT
GTCCAGGCAGGTAGATGACGACCATCAGGGACAGCTTCAAGGATCGCTCGC
GGCTCTTACCAGCCTAACTTCGATCATTGGACCGCTGATCGTCACGGCGAT
TTATGCCGCCTCGGCGAGCACATGGAACGGGTTGGCATGGATTGTAGGCGC
CGCCCTATACCTTGTCTGCCTCCCCGCGTTGCGTCGCGGTGCATGGAGCCG
GGCCACCTCGACCTGAATGGAAGCCGGCGGCACCTCGCTAACGGATTCACC
GTTTTTATCAGGCTCTGGGAGGCAGAATAAATGATCATATCGTCAATTATT
ACCTCCACGGGGAGAGCCTGAGCAAACTGGCCTCAGGCATTTGAGAAGCAC
ACGGTCACACTGCTTCCGGTAGTCAATAAACCGGTAAACCAGCAATAGACA
TAAGCGGCTATTTAACGACCCTGCCCTGAACCGACGACCGGGTCGAATTTG
CTTTCGAATTTCTGCCATTCATCCGCTTATTATCACTTATTCAGGCGTAGC
AACCAGGCGTTTAAGGGCACCAATAACTGCCTTAAAAAAATTACGCCCCGC
CCTGCCACTCATCGCAGTACTGTTGTAATTCATTAAGCATTCTGCCGACAT
GGAAGCCATCACAAACGGCATGATGAACCTGAATCGCCAGCGGCATCAGCA
CCTTGTCGCCTTGCGTATAATATTTGCCCATGGTGAAAACGGGGGCGAAGA
AGTTGTCCATATTGGCCACGTTTAAATCAAAACTGGTGAAACTCACCCAGG
GATTGGCTGAGACGAAAACATATTCTCAATAAACCCTTTAGGGAAATAGG
CCAGGTTTTCACCGTAACACGCCACATCTTGCGAATATATGTGTAGAAACT
GCCGGAAATCGTCGTGGTATTCACTCCAGAGCGATGAAAACGTTTCAGTTT
GCTCATGGAAAACGGTGTAACAAGGGTGAACACTATCCCATATCACCAGCT
CACCGTCTTTCATTGCCATACGGAATTCCGGATGAGCATTCATCAGGCGGG
CAAGAATGTGAATAAAGGCCGGATAAAACTTGTGCTTATTTTTCTTTACGG
TCTTTAAAAAGGCCGTAATATCCAGCTGAACGGTCTGGTTATAGGTACATT
GAGCAACTGACTGAAATGCCTCAAAATGTTCTTTACGATGCCATTGGGATA
TATCAACGGTGGTATATCCAGTGATTTTTTCTCCATTTTAGCTTCCTTAG
CTCCTGAAAATCTCGATAACTCAAAAAATACGCCCGGTAGTGATCTTATTT
CATTATGGTGAAAGTTGGAACCTCTTACGTGCCGATCAACGTCTCATTTTC
GCCAAAAGTTGGCCCAGGGCTTCCCGGTATCAACAGGGACACCAGGATTTA
TTTATTCTGCGAAGTGATCTTCCGTCACAGGTATTTATTCGAAGACGAAAG
GGCCTCGTGATACGCCTATTTTTATAGGTTAATGTCATGATAATAATGGTT
TCTTAGACGTCAGGTGGCACTTTTCGGGGAAATGTGCGCGGAACCCCTATT
TGTTTATTTTTCTAAATACATTCAAATATGTATCCGCTCATGAGACAATAA
```

FIG. 2-3

```
CCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGTTG
GGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTT
CTGCTATGTGGCGCGGTATTATCCCGTGTTGATCCCCACAGCAAGATGCAA
CTTTCGCCAGATACGACGGCGCTCTTTGCCGTGCTTTCTGACTTTCCATTC
GCCTTCACCAAAGACCTTCAGCCCGGTGGAATCAATCACCAGGTGTGCGAT
TTCACCCCGGGTGGACGTTTTGAAACTGACATTAACCGACTTTGCCCGCTT
ACTGACACTGGTGTAATCCGGGCAGCGCAACGGAACGTTCATCAGGGCAAA
AATGGAATCAATAAAACCCTGCGCAGCCCGCAGGGTCAGCCGGAATACGCG
TTTAATCACCAGAACGGTGGTGATGGCGAGATCAGAATAGCGCTGGGGCCT
TCCTCGTGATGAAGGTGTTGCCGACTCATACCAGGCCTGAATCGCCTCATC
ATCCAGCCAGAAAGTGAGGGAGCCACGGTTGATGAGAGCTTTGTTGTAGGT
GGACCAGTTGGTGATTCTGAACTTTTGCTTTGCCACGGAATGGTCTGTGTT
GTCGGGAGGATGCGTGATCTGATCCTTCAACTCAGCAAAAGTTCGATTTAT
TCAACAAAGCCACTTTCAGTATGGATTTGGGTGTTACGGGGGGGGTTGGT
GCTTAAAATCGCGCTGAGGATTTCTGATGGTGTTAAGCGGGCGGTTTTGAG
ATGTAAACTCGCCCGTTTAACATAATGGATCTTGCGCGCACCGCCCGAACA
CCACTCGCCACAAAAAACCGCCGGAACGTCCAAAAGTACGGGTTTTGCTGC
CCGCAAACGGGCTGTTCTGGTGTTGCTAGTTTGTTATCAGAATCGCAGATC
CGGCTTCAGCCGGTTTGCCGGCTGAAAGCGCTATTTCTTCCAGAATTGCCA
TGATTTTTTCCCCACGGGAGGCGTCACTGGCTCCCGTGTTGTCGGCAGCTT
TGATTCGATAAGCAGCATCGCCTGTTTCAGGCTGTCTATGTGTGACTGTTG
AGCTGTAACAAGTTGTCTCAGGTGTTCAATTTCATGTTCTAGTTGCTTTGT
TTTACTGGTTTCACCTGTTCTATTAGGTGTTACATGCTGTTCATCTGTTAC
ATTGTCGATCTGTTCATGGTGAACAGCTTTAAATGCACCAAAAACTCGTAA
AAGCTCTGATGTATCTATCTTTTTACACCGTTTTCATCTGTGCATATGGA
CAGTTTTCCCTTTGATATGTAACGGTGAACAGTTGTTCTACTTTTGTTTGT
TAGTCTTGATGCTTCACTGATAGATACAAGAGCCATAAGAACCTCAGATCC
TTCCGTATTTAGCCAGTATGTTCTCTAGTGTGGTTCGTTGTTTTGCGTGA
GCCATGAGAACGAACCATTGAGATCATACTTACTTTGCATGTCACTCAAAA
```

FIG. 2-4

```
ATTTTGCCTCAAAACTGGTGAGCTGAATTTTTGCAGTTAAAGCATCGTGTA
GTGTTTTTCTTAGTCCGTTATGTAGGTAGGAATCTGATGTAATGGTTGTTG
GTATTTGTCACCATTCATTTTTATCTGGTTGTTCTCAAGTTCGGTTACGA
GATCCATTTGTCTATCTAGTTCAACTTGGAAAATCAACGTATCAGTCGGGC
GGCCTCGCTTATCAACCACCAATTTCATATTGCTGTAAGTGTTTAAATCTT
TACTTATTGGTTTCAAAACCCATTGGTTAAGCCTTTTAAACTCATGGTAGT
TATTTTCAAGCATTAACATGAACTTAAATTCATCAAGGCTAATCTCTATAT
TTGCCTTGTGAGTTTTCTTTTGTGTTAGTTCTTTTAATAACCACTCATAAA
TCCTCATAGAGTATTTGTTTTCAAAAGACTTAACATGTTCCAGATTATATT
TTATGAATTTTTTAACTGGAAAAGATAAGGCAATATCTCTTCACTAAAAA
CTAATTCTAATTTTTCGCTTGAGAACTTGGCATAGTTTGTCCACTGGAAAA
TCTCAAAGCCTTTAACCAAAGGATTCCTGATTTCCACAGTTCTCGTCATCA
GCTCTCTGGTTGCTTTAGCTAATACACCATAAGCATTTTCCCTACTGATGT
TCATCATCTGAACGTATTGGTTATAAGTGAACGATACCGTCCGTTCTTTCC
TTGTAGGGTTTTCAATCGTGGGGTTGAGTAGTGCCACACAGCATAAAATTA
GCTTGGTTTCATGCTCCGTTAAGTCATAGCGACTAATCGCTAGTTCATTTG
CTTTGAAAACAACTAATTCAGACATACATCTCAATTGGTCTAGGTGATTTT
AATCACTATACCAATTGAGATGGGCTAGTCAATGATAATTACTAGTCCTTT
TCCTTTGAGTTGTGGGTATCTGTAAATTCTGCTAGACCTTTGCTGGAAAAC
TTGTAAATTCTGCTAGACCCTCTGTAAATTCCGCTAGACCTTTGTGTGTTT
TTTTTGTTTATATTCAAGTGGTTATAATTTATAGAATAAAGAAAGAATAAA
AAAAGATAAAAAGAATAGATCCCAGCCCTGTGTATAACTCACTACTTTAGT
CAGTTCCGCAGTATTACAAAAGGATGTCGCAAACGCTGTTTGCTCCTCTAC
AAAACAGACCTTAAAACCCTAAAGGCTTAAGTAGCACCCTCGCAAGCTCGG
GCAAATCGCTGAATATTCCTTTTGTCTCCGACCATCAGGCACCTGAGTCGC
TGTCTTTTTCGTGACATTCAGTTCGCTGCGCTCACGGCTCTGGCAGTGAAT
GGGGGTAAATGGCACTACAGGCGCCTTTTATGGATTCATGCAAGGAAACTA
CCCATAATACAAGAAAGCCCGTCACGGGCTTCTCAGGGCGTTTTATGGCG
GGTCTGCTATGTGGTGCTATCTGACTTTTTGCTGTTCAGCAGTTCCTGCCC
TCTGATTTTCCAGTCTGACCACTTCGGATTATCCCGTGACAGGTCATTCAG
ACTGGCTAATGCACCCAGTAAGGCAGCGGTATCATCAACAGGCTTACCCGT
CTTACTGTCGGGGATC
```

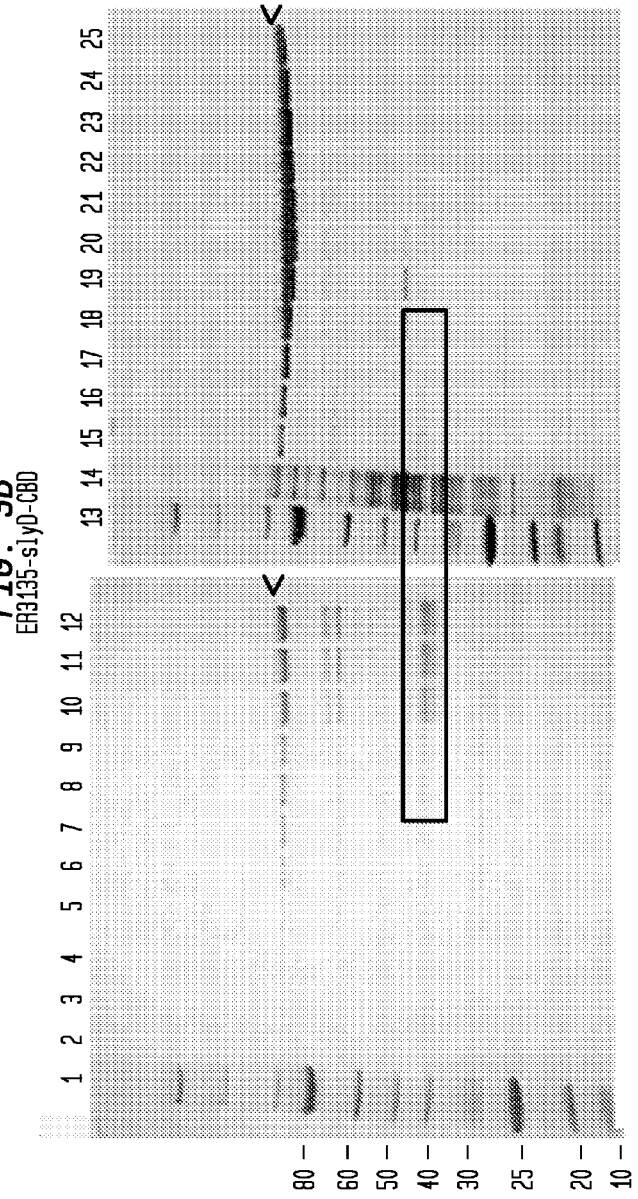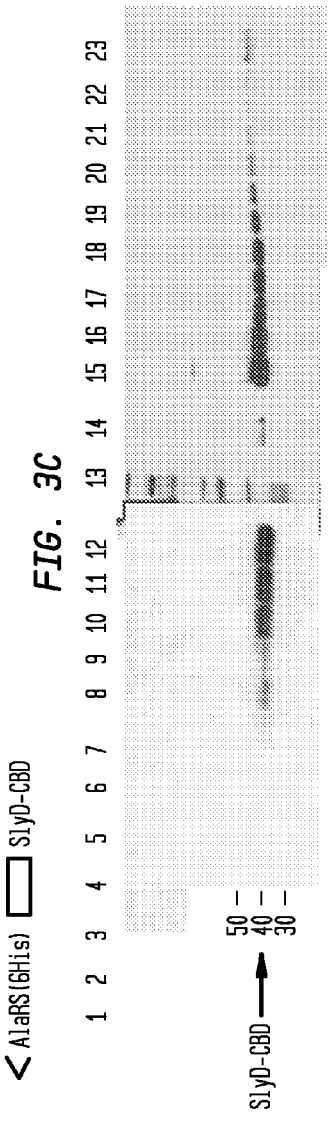
FIG. 3B
FIG. 3C

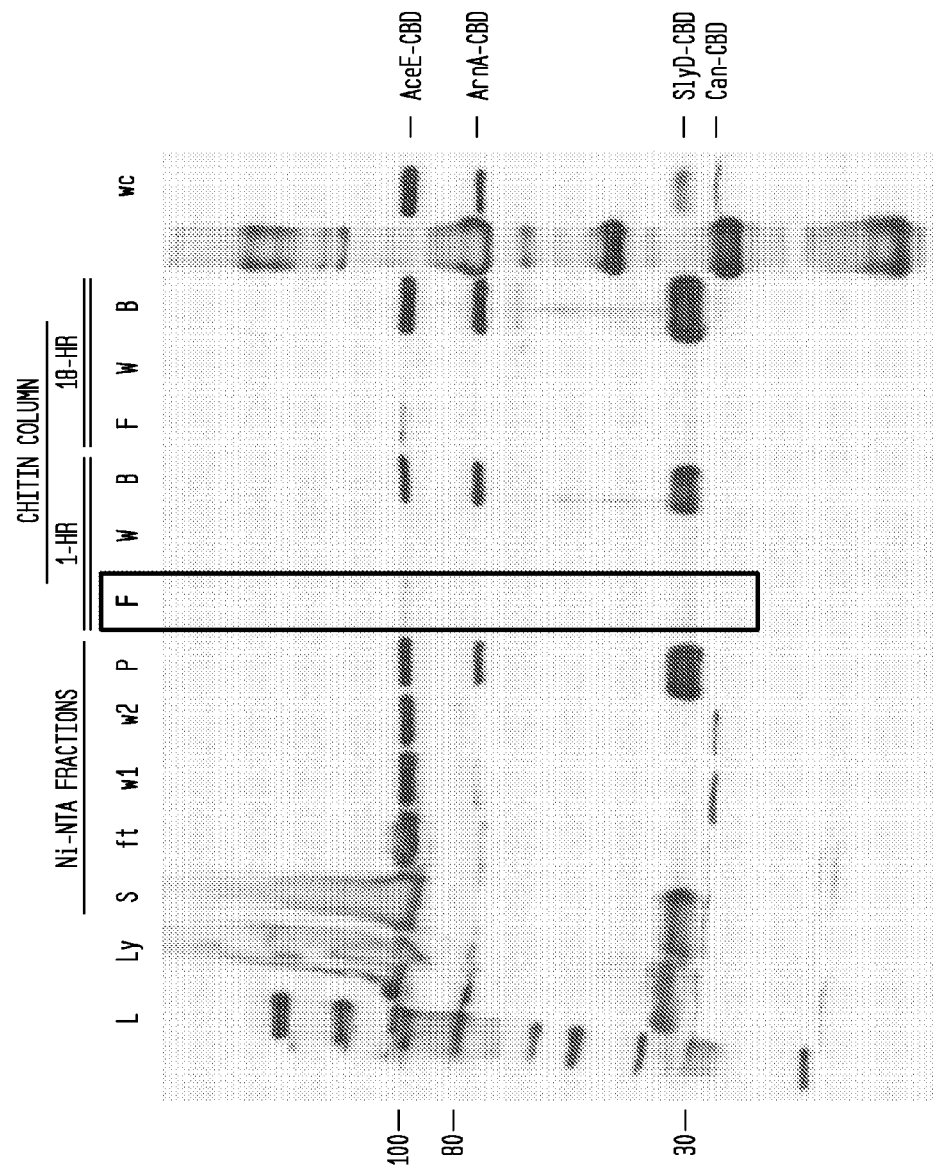

FIG. 8-1

A. aceE-CBD-aceF insert (SEQ ID NO: 50)

AAGCTTGGTACGTTCGTGAACACTTCTTCGGTAAATATCCTGAAACCGCAG
CACTGGTTGCAGACTGGACTGACGAGCAGATCTGGGCACTGAACCGTGGTG
GTCACGATCCGAAGAAAATCTACGCTGCATTCAAGAAAGCGCAGGAAACCA
AAGGCAAAGCGACAGTAATCCTTGCTCATACCATTAAAGGTTACGGCATGG
GCGACGCGGCTGAAGGTAAAAACATCGCGCACCAGGTTAAGAAAATGAACA
TGGACGGTGTGCGTCATATCCGCGACCGTTTCAATGTGCCGGTGTCTGATG
CAGATATCGAAAAACTGCCGTACATCACCTTCCCGGAAGGTTCTGAAGAGC
ATACCTATCTGCACGCTCAGCGTCAGAAACTGCACGGTTATCTGCCAAGCC
GTCAGCCGAACTTCACCGAGAAGCTTGAGCTGCCGAGCCTGCAAGACTTCG
GCGCGCTGTTGGAAGAGCAGAGCAAAGAGATCTCTACCACTATCGCTTTCG
TTCGTGCTCTGAACGTGATGCTGAAGAACAAGTCGATCAAAGATCGTCTGG
TACCGATCATCGCCGACGAAGCGCGTACTTTCGGTATGGAAGGTCTGTTCC
GTCAGATTGGTATTTACAGCCCGAACGGTCAGCAGTACACCCCGCAGGACC
GCGAGCAGGTTGCTTACTATAAAGAAGACGAGAAAGGTCAGATTCTGCAGG
AAGGGATCAACGAGCTGGGCGCAGGTTGTTCCTGGCTGGCAGCGGCGACCT
CTTACAGCACCAACAATCTGCCGATGATCCCGTTCTACATCTATTACTCGA
TGTTCGGCTTCCAGCGTATTGGCGATCTGTGCTGGGCGGCTGGCGACCAGC
AAGCGCGTGGCTTCCTGATCGGCGGTACTTCCGGTCGTACCACCCTGAACG
GCGAAGGTCTGCAGCACGAAGATGGTCACAGCCACATTCAGTCGCTGACTA
TCCCGAACTGTATCTCTTACGACCCGGCTTACGCTTACGAAGTTGCTGTCA
TCATGCATGACGGTCTGGAGCGTATGTACGGTGAAAAACAAGAGAACGTTT
ACTACTACATCACTACGCTGAACGAAAACTACCACATGCCGGCAATGCCGG
AAGGTGCTGAGGAAGGTATCCGTAAAGGTATCTACAAACTCGAAACTATTG
AAGGTAGCAAAGGTAAAGTTCAGCTGCTCGGCTCCGGTTCTATCCTGCGTC
ACGTCCGTGAAGCAGCTGAGATCCTGGCGAAAGATTACGGCGTAGGTTCTG
ACGTTTATAGCGTGACCTCCTTCACCGAGCTGGCGCGTGATGGTCAGGATT
GTGAACGCTGGAACATGCTGCACCCGCTGGAAACTCCGCGCGTTCCGTATA
TCGCTCAGGTGATGAACGACGCTCCGGCAGTGGCATCTACCGACTATATGA
AACTGTTCGCTGAGCAGGTCCGTACTTACGTACCGGCTGACGACTACCGCG
TACTGGGTACTGATGGCTTCGGTCGTTCCGACAGCCGTGAGAACCTGCGTC

FIG. 8-2

```
ACCACTTCGAAGTTGATGCTTCTTATGTCGTGGTTGCGGCGCTGGGCGAAC
TGGCTAAACGTGGCGAAATCGATAAGAAAGTGGTTGCTGACGCAATCGCCA
AATTCAACATCGATGCAGATAAAGTTAACCCGCGTCTGGCGTCGAGCTCGA
ACAACAACAACAATAACAATAACAACAACCTCCAGTCGACGACAAATCCTG
GTGTATCCGCTTGGCAGGTCAACACAGCTTATACTGCGGGACAATTGGTCA
CATATAACGGCAAGACGTATAAATGTTTGCAGCCCCACACCTCCTTGGCAG
GATGGGAACCATCCAACGTTCCTGCCTTGTGGCAGCTTCAATAAGAGGTAA
AAGAATAATGGCTATCGAAATCAAAGTACCGGACATCGGGGCTGATGAAGT
TGAAATCACCGAGATCCTGGTCAAAGTGGGCGACAAAGTTGAAGCCGAACA
GTCGCTGATCACCGTAGAAGGCGACAAAGCCTCTATGGAAGTTCCGTCTCC
GCAGGCGGGTATCGTTAAAGAGATCAAAGTCTCTGTTGGCGATAAAACCCA
GACCGGCGCACTGATTATGATTTTCGATTCCGCCGACGGTGCAGCAGACGC
TGCACCTGCTCAGGCAGAAGAGAAGAAAGAAGCAGCTCCGGCAGCAGCACC
AGCGGCTGCGGCGGCAAAAGACGTTAACGTTCCGGATATCGGCAGCGACGA
AGTTGAAGTGACCGAAATCCTGGTGAAAGTTGGCGATAAAGTTGAAGCTGA
ACAGTCGCTGATCACCGTAGAAGGCGACAAGGCTTCTATGGAAGTTCCGGC
TCCGTTTGCTGGCACCGTGAAAGAGATCAAAGTGAACGTGGGTGACAAAGT
GTCTACCGGCTCGCTGATTATGGTCTTCGAAGTCGCGGGTGAAGCAGGCGC
GGCAGCTCCGGCCGCTAAACAGGAAGCAGCTCCGGCAGCGGCCCCTGCACC
AGCGGCTGGCGTGAAAGAAGTTAACGTTCCGGATATCGGCGGTGACGAAGT
TGAAGTGACTGAAGTGATGGTGAAAGTGGGCGACAAAGTTGCCGCTGAACA
GTCACTGATCACCGTAGAAGGCGACAAAGCTTCTATGGAAGTTCCGGCGCC
GTTTGCAGGCGTCGTGAAGGAACTGAAAGTCAACGTTGGCGATAAAGTGAA
AACTGGCTCGCTGATTATGATCTTCGAAGTTGAAGGCGCAGCGCCTGCGGC
AGCTCCTGCGAAACAGGAAGCGGCAGCGCCGGCACCGGCAGCAAAAGCTGA
AGCCCCGGCAGCAGCACCAGCTGCGAAAGCGGAAGGCAAATCTGAATTTGC
TGAAAACGACGCTTATGTTCACGCGACTCCGCTGATCCGCCGTCTGGCACG
CGAGTTTGGTGTTAACCTTGCGAAAGTGAAGGGCACTGGCCGTAAAGGTCG
TATCCTGCGCGAAGACGTTCAGGCTTACGTGAAAGAAGCTATCAAACGTGC
AGAAGCAGCTCCGGCAGCGACTGGCGGTGGTATCCCTGGCATGCTGCCGTG
GCCGAAGGTGGACTTCAGCAAGTTTGGTGAAATCGAAGAAGTGGAACTGGG
CCGCATCCAGAAAATCTCTGGTGCGAACCTGAGCCGTAACTGGGTAATGAT
```

FIG. 8-3

CCCGCATGTTACTCACTTCGACAAAACCGATATCACCGAGTTGGAAGCGTT
CCGTAAACAGCAGAACGAAGAAGCGGCGAAACGTAAGCTGGATGTGAAGAT
CACCCCGGTTGTCTTCATCATGAAAGCCGTTGCTGCAGCTCTTGAGCAGAT
GCCTCGCTTCAATAGTTCGCTGTCGGAAGACGGTCAGCGTCTGACCCTGAA
GAAATACATCAACATCGGTGTGGCGGTGGATACCCCGAACGGTCTGGTTGT
TCCGGTATTCAAAGACGTCAACAAGAAGGCATCATCGAGCTGTCTCGCGA
GCTGATGACTATTTCTAAGAAAGCGCGTGACGGTAAGCTGACTGCGGGCGA
AATGCAGGGCGGTTGCTTCACCATCTCCAGCATCGGCGGCCTGGGTACTAC
CCACTTCGCGCCGATTGTGAACGCGCCGGAAGTGGCTATCCTCGGCGTTTC
CAAGTCCGCGATGGAGCCGGTGTGGAATGGTAAAGAGTTCGTGCCGCGTCT
GATGCTGCCGATTTCTCTCCTTCGACCACCGCGTGATCGACGGTGCTGA
TGGTGCCCGTTTCATTACCATCATTAACAACACGCTGTCTGACATTCGCCG
TCTGGTGATGTAAGTAAAAGAGCCGGCCCAACGGCCGGCTTTTTTCTGGTA
ATCTCATGAATGTATTGAGGTTATTAGCGAATAGACAAAgcggccgc B. arnA-CBD-arnD insert (SEQ ID NO: 51)

AAGCTTACTCGGTGAATATATCGGCAGGATCTACACCGATGTCCGCGCCCG
CCCCCGCTATTTTGTTCAGCAAGTTATCCGTCCATCCAGCAAGGAAAATGA
ATAATGAAAACCGTCGTTTTTGCCTACcACGATATGGGATGCCTCGGTATT
GAAGCCCTGCTGGCTGCCGGTTACGAAATTAGCGCCATTTTTACCCATACT
GATAATCCCGGTGAAAAAGCCTTTTATGGTTCGGTGGCTCGTCTGGCGGCG
GAAAGAGGCATTCCGGTTTATGCGCCGGATAACGTTAATCATCCGCTGTGG
GTGGAACGCATTGCCCAACTGTCGCCAGATGTGATTTTCTCTTTTTATTAT
CGCCATCTTATTTACGACGAAATTTTGCAGCTCGCTCCCGCAGGTGCATTT
AATCTGCATGGTTCGCTGTTACCAAAATATCGTGGTCGCGCGCCGCTGAAC
TGGGTGCTGGTCAACGGTGAAACGGAAACTGGCGTTACATTGCACCGAATG
GTGAAACGTGCCGATGCCGGGGCCATTGTGGCGCAACTGCGCATTGCCATT
GCGCCAGACGATATCGCTATTACGCTGCATCATAAATTGTGCCATGCCGCG
CGCCAGCTACTGGAACAGACATTACCCGCCATTAAACACGGTAATATTCTG
GAAATCGCCCAGCGCGAAAACGAAGCCACCTGTTTTGGTCGCAGAACGCCG
GATGACAGTTTCCTTGAATGGCATAAACCGGCATCCGTACTGCACAACATG

FIG. 8-4

```
GTACGTGCCGTTGCCGATCCGTGGCCGGGTGCCTTCAGCTATGTTGGCAAT
CAGAAATTCACCGTCTGGTCGTCGCGTGTTCATCCTCATGCCAGCAAAGCA
CAGCCGGGGAGCGTGATTTCTGTTGCGCCACTGCTGATTGCCTGTGGCGAT
GGCGCGCTGGAAATCGTCACCGGACAGGCGGGCGACGGCATTACTATGCAG
GGCTCGCAATTAGCGCAGACGCTGGGCCTGGTGCAAGGTTCACGCTTGAAT
AGCCAGCCTGCCTGCACCGCCCGACGCCGTACCCGGGTACTCATCCTCGGG
GTGaATGGCTTTATTGGCAACCATCTGACAGAACGCCTGCTGCGCGAAGAT
CATTATGAAGTTTACGGTCTGGATATTGGCAGCGATGCGATAAGCCGTTTT
CTGAATCATCCGCATTTTCACTTTGTTGAAGGCGATATCAGTATTCATTCC
GAATGGATTGAGTATCATGTCAAAAAATGTGATGTCGTCTTGCCGCTGGTG
GCGATAGCCACGCCGATTGAATATACCCGCAACCCGCTGCGCGTATTTGAA
CTCGATTTTGAAGAGAATCTGCGCATTATCCGCTACTGCGTGAAGTACCGT
AAGCGAATCATCTTCCCGTCAACTTCAGAAGTTTATGGGATGTGTAGCGAT
AAATACTTCGATGAGGACCATTCTAATTTAATCGTCGGCCCGGTGAATAAA
CCACGCTGGATTTATTCGGTATCAAAACAATTACTTGATCGGGTGATCTGG
GCCTATGGCGAAAAAGAGGGTTTACAGTTCACCCTCTTCCGCCCGTTTAAC
TGGATGGGACCACGACTGGATAACCTTAATGCAGCGCGAATTGGCAGCTCC
CGCGCTATTACGCAACTCATTCTCAATCTGGTAGAAGGTTCACCGATTAAG
CTGATTGATGGCGGAAAACAAAAACGCTGCTTTACTGATATTCGCGATGGT
ATCGAGGCGTTATACCGCATTATCGAAAATGCGGGAAATCGCTGCGACGGT
GAAATTATCAACATTGGCAATCCTGAGAACGAAGCGAGCATTGAGGAACTG
GGCGAGATGCTGCTGGCGAGCTTCGAAAAACATCCGCTGCGCCATCATTTC
CCACCGTTTGCGGGCTTTCGCGTTGTCGAAAGTAGCAGCTACTACGGCAAA
GGATATCAGGACGTAGAGCATCGTAAACCGAGCATCCGCAATGCCCACCGC
TGCCTGGACTGGGAGCCGAAAATTGATATGCAGGAAACCATCGACGAAACG
CTGGATTTCTTCCTGCGCACCGTTGATCTTACGGATAAACCTTCCCTGCAG
GCTTCGAGCTCGAACAACAACAACAATAACAATAACAACAACCTCCAGTCG
ACGACAAATCCTGGTGTATCCGCTTGGCAGGTCAACACAGCTTATACTGCG
GGACAATTGGTCACATATAACGGCAAGACGTATAAATGTTTGCAGCCCCAC
ACCTCCTTGGCAGGATGGGAACCATCCAACGTTCCTGCCTTGTGGCAGCTT
CAAGATAAACCATCATGACCAAAGTAGGCTTACGCATTGATGTCGATACCT
TTCGTGGCACCCGTGAAGGCGTGCCGCGTCTGCTGGAAATCTTGAGTAAGC
```

FIG. 8-5

ATAATATTCAGGCCAGCATTTTTTTCAGCGTCGGCCCGGACAATATGGGCC
GCCATCTCTGGCGACTGGTGAAGCCACAGTTTTTGTGGAAGATGCTGCGCT
CAAACGCGGCATCGCTTTATGGCTGGGATATTTTACTGGCAGGTACGGCCT
GGCCAGGTAAAGAGATTGGTCATGCCAATGCCGATATCATTCGTGAAGCGG
CTAAACATCACGAAGTCGGCCTGCACGCCTGGGATCACCATGCCTGGCAAG
CCCGTAGCGGTAACTGGGATCGGCAAACAATGATCGACGATATTGCACGCG
GTCTTCGCACTCTGGAAGAGATTATCGGTCAACCGGTAACCTGTTCTGCCG
CTGCGGGCTGGCGTGCCGACCAGAAGGTGATCGAAGCAAAAGAAGCGTTCC
ATTTGCGCTACAACAGCGATTGTCGTGGGGCCATGCCGTTCCGTCCATTGC
TCGAATCAGGAAACCCTGGCACTGCGCAAATTCCGGTGACGGTACC

C. can-CBD insert (SEQ ID NO: 52)

AAGCTTCGAGATCGTAACCAAATACGCTGACCCGCCCGGAGGTTTTATTTA
CCAGAGAGCTGATAATACCGATAGTGGTCGATTTCCCGGCCCCGTTCGGCC
CGAGAAGCGCATAAAAATCACCCGCTTCGACCTGCAAATCTATCCCACGAA
GCGCCTGAACGCCGCCTGGATAGGTTTTTTTAAGCTGTTGAAGTTCCAGTG
CAATGGTCATAAATTTTTACTTACCTTACGTTCTTACACTTTATCTGTGGT
TTAAATCGTCCCGGAGTTGCCCTATATTAGCCAAACGTAATTATTTGGTTA
CAGGTCGTTAACCTCCATGAAAGACATAGATACACTCATCAGCAACAATGC
ACTATGGTCAAAAATGCTGGTGGAAGAGGATCCCGGGTTTTTTGAGAAACT
GGCACAAGCGCAAAAACCGCGCTTTCTATGGATTGGATGTTCCGACAGTCG
CGTTCCTGCAGAACGTTTAACCGGTCTTGAGCCGGGCGAACTCTTTGTTCA
CCGTAATGTTGCTAACCTGGTCATTCACACTGACCTGAACTGCCTTTCCGT
GGTTCAGTATGCAGTGGATGTACTCGAAGTTAACACATTATTATCTGTGG
CCACTACGGTTGCGGCGGCGTACAAGCCGCAGTTGAAAACCCGGAACTGGG
GCTTATCAACAACTGGCTGCTGCATATCCGCGATATCTGGTTCAAACATAG
CTCATTGCTCGGCGAAATGCCGCAAGAGCGCCGTCTGGATACCTTGTGTGA
ACTGAACGTCATGGAACAGGTGTATAACCTGGGCCACTCCACCATTATGCA
ATCAGCGTGGAAACGCGGGCAGAAAGTTACCATTCACGGCTGGGCCTACGG
CATTCACGACGGCTTGCTGCGTGATCTGGATGTTACCGCCACCAACCGCGA
AACCCTTGAGCAACGTTACCGTCACGGGATTTCCAACCTCAAGCTGAAACA

FIG. 8-6

CGCCAACCACAAATCGAGCTCGAACAACAACAACAATAACAATAACAACAA
CCTCCAGTCGACGACAAATCCTGGTGTATCCGCTTGGCAGGTCAACACAGC
TTATACTGCGGGACAATTGGTCACATATAACGGCAAGACGTATAAATGTTT
GCAGCCCCACACCTCCTTGGCAGGATGGGAACCATCCAACGTTCCTGCCTT
GTGGCAGCTTCAATAAGCGATCGCAAATGCCATGCCGGATGCAACACATCC
GGCAACTTCACACTTACTCGTCCAGCAGAATCACTTTGCCGATATACGGCA
GATGACGGTAACGCTGTGCGTAATCAATGCCGTAACCCACCACAAACTCAT
CCGGGATCGAGAAACCGATAAATTCTACCGGGACGTTCACTTCACGACGGG
ACGGTTTATCCAGCAGCGTACAAATCGCCAGCGACTTCGGTTCGCGCAGGC
TTAAGATCTCACGCACTTTCGACAGTGTATTCCCCGAGTCGATGATATCTT
CAACAATCAGCACGTCCTTGCCACGGATATCTTCATCCAGATCTTTGAGGA
TTTTCACATCACGGGTGGTGGACATGCCGCTACCGTAGCTGGAGGCGGTCA
TAAAGTCGACTTCATGAGATACCTGAACTTCACGGCACAGGTCCGCCATAA
ACATAAATGAGCCACGCAGCAGACCCACCAGCACCATATCGCTGCCGCTGT
CTTTGTAACGCTCAGTAATCTGACGACCCAGTTCGGCGATACGCGCTTTAA
TCTCCGCTTCGGGGATCATTACTTCTACAGTATGTTTCATATCTCTAACCA
TATGCGGCCG

D. slyD-CBD insert (SEQ ID NO: 53)

AAGCTTGTTAAGTGCGGACATCAGATGCGAGAAGCAGACAAAGAAGCCCGC
GATCACGTTCGCAAAGATGAGCAAGTGATCGGGATTTTTCATCCGGACTAG
CGATATGCGCCGAGTTTTTTTAAGCTAGTGAGTACACGGCTGCAGAATTCC
GCTACAATCTGCGCCACTATTCTTCCCATGCTCAGGAGATATCATGAAAGT
AGCAAAAGACCTGGTGGTCAGCCTGGCCTATCAGGTACGTACAGAAGACGG
TGTGTTGGTTGATGAGTCTCCGGTGAGTGCGCCGCTGGACTACCTGCATGG
TCACGGTTCCCTGATCTCTGGCCTGGAAACGGCGCTGGAAGGTCATGAAGT
TGGCGACAAATTTGATGTCGCTGTTGGCGCGAACGACGCTTACGGTCAGTA
CGACGAAAACCTGGTGCAACGTGTTCCTAAAGACGTATTTATGGGCGTTGA
TGAACTGCAGGTAGGTATGCGTTTCCTGGCTGAAACCGACCAGGGTCCGGT
ACCGGTTGAAATCACTGCGGTTGAAGACGATCACGTCGTGGTTGATGGTAA
CCACATGCTGGCCGGTCAGAACCTGAAATTCAACGTTGAAGTTGTGGCGAT

FIG. 8-7

```
TCGCGAAGCGACTGAAGAAGAACTGGCTCATGGTCACGTTCACGGCGCGCA
CGATCACCACCACGATCACGACCACGACGGTTGCTGCGGCGGTCATGGCCA
CGATCACGGTCATGAACACGGTGGCGAAGGCTGCTGTGGCGGTAAAGGCAA
CGGCGGTTGCGGTTGCCACCTGCAGGCTTCGAGCTCGAACAACAACAACAA
TAACAATAACAACAACCTCCAGTCGACGACAAATCCTGGTGTATCCGCTTG
GCAGGTCAACACAGCTTATACTGCGGGACAATTGGTCACATATAACGGCAA
GACGTATAAATGTTTGCAGCCCCACACCTCCTTGGCAGGATGGGAACCATC
CAACGTTCCTGCCTTGTGGCAGCTTCAATAAGCGATCGCATACCGAAAAAG
TGACAAAAAAGCGGGGAATCCCCGCTTTTTTTACGCCTCAATAATGTGGCG
GTGGCGTTTCTTCAGCCTGCGACGCGATGTTCGACGGCTGGCTGGCTTTTA
ACTTCTCGGTCAGCAGACGCAGATGATCGCGCAGTTTCGCCATCTCCATTT
CATGAGCGGTCACCGTGACGTTCAGTTCTTCAATGGTGATTTCCTGAAAAG
CCAGTCGGCTCTCCAGCTCTGCCAGGCGTGCTTCCAATGATAAATCCTGCA
TGATTCACCTCTTTTGTCGAATGGTCGCCGCGGATTCTACTTAACTTTGCT
GCCCGAGACAGCACTCATTTCGCGGTCATCGAAACTAATTTAAACAAAAAG
AGTCTGAAAATAGATGATAATAGGGCGTGTCTGTATGTAGATTTGTTCGAC
AACGCTTTATAGTACCCTTCTGATAATAGTTAACCCTGGGGTGAGATGCCC
CGATCCTGGAGATATGGATGAAATCACTGTTTAAAGTAACGCTGCTGGCGA
CCACAATGGCCGTTGCCCTGCATGCACCAATCACTTTTGCTGCTGAAGCTG
CCGGCCG
```

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Asp Tyr Lys Asp Asp Asp Asp Lys
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Trp Ser His Pro Gln Phe Glu Lys
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Gly Leu Asn Asp Ile Phe Glu Ala Gln Lys Ile Glu Trp His
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Synthetic Construct

<400> SEQUENCE: 4

Leu Gln Ala Ser Ser Ser Asn Asn Asn Asn Asn Asn Asn Asn Asn
1               5                   10                  15

Leu Gln Ser

<210> SEQ ID NO 5
<211> LENGTH: 30
<212> TYPE: DNA
<213> ORGANISM: Artificial Sequence
<220> FEATURE:
<223> OTHER INFORMATION: Synthetic Construct

<400> SEQUENCE: 5
ccaccaaagc ttgttaagtg cggacatcag                                   30

<210> SEQ ID NO 6
<211> LENGTH: 32
<212> TYPE: DNA
<213> ORGANISM: Artificial Sequence
<220> FEATURE:
<223> OTHER INFORMATION: Synthetic Construct

<400> SEQUENCE: 6
ggtggtcctg caggtggcaa ccgcaaccgc cg                                32

<210> SEQ ID NO 7
<211> LENGTH: 39
<212> TYPE: DNA
<213> ORGANISM: Artificial Sequence
<220> FEATURE:
<223> OTHER INFORMATION: Synthetic Construct

<400> SEQUENCE: 7
ccaccagcga tcgcataccg aaaaagtgac aaaaaagcg                         39
```

```
<210> SEQ ID NO 8
<211> LENGTH: 34
<212> TYPE: DNA
<213> ORGANISM: Artificial Sequence
<220> FEATURE:
<223> OTHER INFORMATION: Synthetic Construct

<400> SEQUENCE: 8
ggtggtcggc cggcagcttc agcagcaaaa gtga                              34

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct

<400> SEQUENCE: 9
agcggataac aatttcacac agga                                        24

<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10
gcacccagtg cataagctga tttct                                       25

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
cgccagggtt ttcccagtca cgac                                        24

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
gcctgtcagg cgcaggattc a                                           21

<210> SEQ ID NO 13
<211> LENGTH: 41
<212> TYPE: DNA
<213> ORGANISM: Artificial Sequence
<220> FEATURE:
<223> OTHER INFORMATION: Synthetic Construct

<400> SEQUENCE: 13
accaccgcga tcgcaaatgc catgccggat gcaacacatc c                     41

<210> SEQ ID NO 14
<211> LENGTH: 38
<212> TYPE: DNA
<213> ORGANISM: Artificial Sequence
<220> FEATURE:
<223> OTHER INFORMATION: Synthetic Construct
```

```
<400> SEQUENCE: 14
accacccggc cgcatatggt tagagatatg aaacatac                                38

<210> SEQ ID NO 15
<211> LENGTH: 35
<212> TYPE: DNA
<213> ORGANISM: Artificial Sequence
<220> FEATURE:
<223> OTHER INFORMATION: Synthetic Construct

<400> SEQUENCE: 15
accaccaagc ttcgagatcg taaccaaata cgctg                                  35

<210> SEQ ID NO 16
<211> LENGTH: 41
<212> TYPE: DNA
<213> ORGANISM: Artificial Sequence
<220> FEATURE:
<223> OTHER INFORMATION: Synthetic Construct

<400> SEQUENCE: 16
accaccgagc tcgatttgtg gttggcgtgt ttcagcttga g                           41

<210> SEQ ID NO 17
<211> LENGTH: 26
<212> TYPE: DNA
<213> ORGANISM: Artificial Sequence
<220> FEATURE:
<223> OTHER INFORMATION: Synthetic Construct

<400> SEQUENCE: 17
cgagtaatcg tcgcgagcct gtattg                                            26

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
gataaaccat catgaccaaa gtagg                                             25

<210> SEQ ID NO 19
<211> LENGTH: 28
<212> TYPE: DNA
<213> ORGANISM: Artificial Sequence
<220> FEATURE:
<223> OTHER INFORMATION: Synthetic Construct

<400> SEQUENCE: 19
caggtgggta ccgtcaccgg aatttgcg                                          28

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
gatattgctg ggtaccgagc tcgaa                                             25
```

```
<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
ttgaagctgc cacaaggcag gaacg                                    25

<210> SEQ ID NO 22
<211> LENGTH: 30
<212> TYPE: DNA
<213> ORGANISM: Artificial Sequence
<220> FEATURE:
<223> OTHER INFORMATION: Synthetic Construct

<400> SEQUENCE: 22
cggcataagc ttactcggtg aatatatcgg                               30

<210> SEQ ID NO 23
<211> LENGTH: 39
<212> TYPE: DNA
<213> ORGANISM: Artificial Sequence
<220> FEATURE:
<223> OTHER INFORMATION: Synthetic Construct

<400> SEQUENCE: 23
agcctgcagg gaaggtttat ccgtaagatc aacggtgcg                     39

<210> SEQ ID NO 24
<211> LENGTH: 22
<212> TYPE: DNA
<213> ORGANISM: Artificial Sequence
<220> FEATURE:
<223> OTHER INFORMATION: Synthetic Construct

<400> SEQUENCE: 24
gatgtacgac ctggtgacct gc                                       22

<210> SEQ ID NO 25
<211> LENGTH: 22
<212> TYPE: DNA
<213> ORGANISM: Artificial Sequence
<220> FEATURE:
<223> OTHER INFORMATION: Synthetic Construct

<400> SEQUENCE: 25
ggatgcggtt gagtaaccaa cc                                       22

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
taagaggtaa aagaataatg                                          20

<210> SEQ ID NO 27
<211> LENGTH: 39
<212> TYPE: DNA
<213> ORGANISM: Artificial Sequence
<220> FEATURE:
<223> OTHER INFORMATION: Synthetic Construct
```

<400> SEQUENCE: 27
accaccgcat gcgaattgct ctattcgcgt cgcgagatg                                    39

<210> SEQ ID NO 28
<211> LENGTH: 41
<212> TYPE: DNA
<213> ORGANISM: Artificial Sequence
<220> FEATURE:
<223> OTHER INFORMATION: Synthetic Construct

<400> SEQUENCE: 28
accaccgagc tcgacgccag acgcgggtta actttatctg c                                 41

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
gaggtaaaag aataatggct atcg                                                   24

<210> SEQ ID NO 30
<211> LENGTH: 29
<212> TYPE: DNA
<213> ORGANISM: Artificial Sequence
<220> FEATURE:
<223> OTHER INFORMATION: Synthetic Construct

<400> SEQUENCE: 30
caaacggcgg ccgctttgtc tattcgcta                                              29

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
cagctccggc cgacgcgctg ggct                                                   24

<210> SEQ ID NO 32
<211> LENGTH: 24
<212> TYPE: DNA
<213> ORGANISM: Artificial Sequence
<220> FEATURE:
<223> OTHER INFORMATION: Synthetic Construct

<400> SEQUENCE: 32
ttattgaagc tgccacaagg cagg                                                   24

<210> SEQ ID NO 33
<211> LENGTH: 12
<212> TYPE: DNA
<213> ORGANISM: Artificial Sequence
<220> FEATURE:
<223> OTHER INFORMATION: Synthetic Construct

<400> SEQUENCE: 33
gctcctctgg ct                                                                12

```
<210> SEQ ID NO 34
<211> LENGTH: 12
<212> TYPE: DNA
<213> ORGANISM: Artificial Sequence
<220> FEATURE:
<223> OTHER INFORMATION: Synthetic Construct

<400> SEQUENCE: 34
catcctctgc at                                                              12

<210> SEQ ID NO 35
<211> LENGTH: 14
<212> TYPE: DNA
<213> ORGANISM: Artificial Sequence
<220> FEATURE:
<223> OTHER INFORMATION: Synthetic Construct

<400> SEQUENCE: 35
gctgacattg tggc                                                            14

<210> SEQ ID NO 36
<211> LENGTH: 15
<212> TYPE: DNA
<213> ORGANISM: Artificial Sequence
<220> FEATURE:
<223> OTHER INFORMATION: Synthetic Construct

<400> SEQUENCE: 36
catgacattg tgcat                                                           15

<210> SEQ ID NO 37
<211> LENGTH: 12
<212> TYPE: DNA
<213> ORGANISM: Artificial Sequence
<220> FEATURE:
<223> OTHER INFORMATION: Synthetic Construct

<400> SEQUENCE: 37
aaagctgccg cg                                                              12

<210> SEQ ID NO 38
<211> LENGTH: 12
<212> TYPE: DNA
<213> ORGANISM: Artificial Sequence
<220> FEATURE:
<223> OTHER INFORMATION: Synthetic Construct

<400> SEQUENCE: 38
aaacatcacg cg                                                              12

<210> SEQ ID NO 39
<211> LENGTH: 31
<212> TYPE: DNA
<213> ORGANISM: Artificial Sequence
<220> FEATURE:
<223> OTHER INFORMATION: Synthetic Construct

<400> SEQUENCE: 39
ggaggaaagc ttgactcaga aagaaggctg g                                         31

<210> SEQ ID NO 40
<211> LENGTH: 40
<212> TYPE: DNA
<213> ORGANISM: Artificial Sequence
<220> FEATURE:
<223> OTHER INFORMATION: Synthetic Construct
```

<400> SEQUENCE: 40
ccaccagagc tcttattact caaccgtaac cgattttgcc                40

<210> SEQ ID NO 41
<211> LENGTH: 24
<212> TYPE: DNA
<213> ORGANISM: Artificial Sequence
<220> FEATURE:
<223> OTHER INFORMATION: Synthetic Construct

<400> SEQUENCE: 41
ggagcttctt ccgctgcctg agcc                                 24

<210> SEQ ID NO 42
<211> LENGTH: 28
<212> TYPE: DNA
<213> ORGANISM: Artificial Sequence
<220> FEATURE:
<223> OTHER INFORMATION: Synthetic Construct

<400> SEQUENCE: 42
tctggctggc ggcaccggta ttgctcat                             28

<210> SEQ ID NO 43
<211> LENGTH: 31
<212> TYPE: DNA
<213> ORGANISM: Artificial Sequence
<220> FEATURE:
<223> OTHER INFORMATION: Synthetic Construct

<400> SEQUENCE: 43
atgtcagctt caatggaggc atccagacct t                         31

<210> SEQ ID NO 44
<211> LENGTH: 33
<212> TYPE: DNA
<213> ORGANISM: Artificial Sequence
<220> FEATURE:
<223> OTHER INFORMATION: Synthetic Construct

<400> SEQUENCE: 44
tgtggctggt ctgcaggcgt tgccgagccg tat                       33

<210> SEQ ID NO 45
<211> LENGTH: 21
<212> TYPE: DNA
<213> ORGANISM: Artificial Sequence
<220> FEATURE:
<223> OTHER INFORMATION: Synthetic Construct

<400> SEQUENCE: 45
agctttgtca gagaaatctt c                                    21

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
cacgcgctgt tcctgggccg t                                    21

<210> SEQ ID NO 47
<211> LENGTH: 21
<212> TYPE: DNA
<213> ORGANISM: Artificial Sequence
<220> FEATURE:
<223> OTHER INFORMATION: Synthetic Construct

<400> SEQUENCE: 47

| atgtttgtca gagaaatctt c | 21 |

<210> SEQ ID NO 48
<211> LENGTH: 30
<212> TYPE: DNA
<213> ORGANISM: Artificial Sequence
<220> FEATURE:
<223> OTHER INFORMATION: Synthetic Construct

<400> SEQUENCE: 48

| gccgcgctgt tcctgggccg tggcgatcag | 30 |

<210> SEQ ID NO 49
<211> LENGTH: 6382
<212> TYPE: DNA
<213> ORGANISM: Artificial Sequence
<220> FEATURE:
<223> OTHER INFORMATION: synthetic construct

<400> SEQUENCE: 49

| gacgctctcc cttatgcgac tcctgcatta ggaagcagcc cagtagtagg ttgaggccgt | 60 |
| tgagcaccgc cgccgcaagg aatggtgcca atacgcaaac cgcctctccc cgcgcgttgg | 120 |
| ccgattcatt aatgcagctg gcacgacagg tttcccgact ggaaagcggg cagtgagcgc | 180 |
| aacgcaatta atgtgagtta gctcactcat taggcacccc aggctttaca ctttatgctt | 240 |
| ccggctcgta tgttgtgtgg aattgtgagc ggataacaat ttcacacagg aaacagctat | 300 |
| gaccatgatt acgccaagct tgcatgcctg caggcttcga gctcgaacaa caacaacaat | 360 |
| aacaataaca acaacctcca gtcgacgaca atcctggtg tatccgcttg gcaggtcaac | 420 |
| acagcttata ctgcgggaca attggtcaca tataacggca agacgtataa atgtttgcag | 480 |
| ccccacacct ccttggcagg atgggaacca tccaacgttc ctgccttgtg gcagcttcaa | 540 |
| gctgaacatg cctttttttcg taagtaagca acataagctg tcacgttttg tgatggctat | 600 |
| tagaaattcc tatgcaacaa ctgaaaaaaa attacaaaaa gtgctttctg aactgaacaa | 660 |
| aaaagagtaa agttagtcgc gtagggtaca gaggtaagat gttctatctt tcagaccttt | 720 |
| tacttcacgt aatcggattt ggctgaatat tttagccgcc ccagtcagta atgactgggg | 780 |
| cgtttttttat tgggcgaaag aaaagatccg taatgcctga tgcgctatgt ttatcaggcc | 840 |
| aacggtagaa ttgtaatcta ttgaatttac gggccggata cgccacatcc ggcacaagca | 900 |
| ttaaggcaag aaaattattc gccgtcctgc gtttcttcta caggctgcat ctcgctaaac | 960 |
| caggtatcca gtttctgccg cagcttgtcc acgccttgtt tcttcaacga agaaaacgtt | 1020 |
| tcaacctgca catcaccgtt aaacgccagt acagcttcac gcaccatatt caattgcgct | 1080 |
| ttacgtgcgc cgcttgccag tttgtccgct tggtcagca gcaccagaac ggcgatattg | 1140 |
| ctgggtaccg agctcgaatt cactggccgt cgttttacaa cgtcgtgact gggaaaaccc | 1200 |
| tggcgttacc caacttaatc gccttgcagc acatccccct ttcgccagct ggcgtaatag | 1260 |
| cgaagaggcc cgcaccgatc gcccttccca acagttgcgc agcctgaatg gcgaatgagc | 1320 |
| ttatcgatga taagctgtca acatggcct gtcgcttgcg gtattcggaa tcttgcacgc | 1380 |

-continued

```
cctcgctcaa gccttcgtca ctggtcccgc caccaaacgt ttcggcgaga agcaggccat    1440
tatcgccggc atggcggccg acgcgctggg ctacgtcttg ctggcgttcg cgacgcgagg    1500
ctggatggcc ttccccatta tgattcttct cgcttccggc ggcatcggga tgcccgcgtt    1560
gcaggccatg ctgtccaggc aggtagatga cgaccatcag ggacagcttc aaggatcgct    1620
cgcggctctt accagcctaa cttcgatcat tggaccgctg atcgtcacgg cgatttatgc    1680
cgcctcggcg agcacatgga acgggttggc atggattgta ggcgccgccc tataccttgt    1740
ctgcctcccc gcgttgcgtc gcggtgcatg gagccgggcc acctcgacct gaatggaagc    1800
cggcggcacc tcgctaacgg attcaccgtt tttatcaggc tctgggaggc agaataaatg    1860
atcatatcgt caattattac ctccacgggg agagcctgag caaactggcc tcaggcattt    1920
gagaagcaca cggtcacact gcttccggta gtcaataaac cggtaaacca gcaatagaca    1980
taagcggcta tttaacgacc ctgccctgaa ccgacgaccg ggtcgaattt gctttcgaat    2040
ttctgccatt catccgctta ttatcactta ttcaggcgta gcaaccaggc gtttaagggc    2100
accaataact gccttaaaaa aattacgccc cgccctgcca ctcatcgcag tactgttgta    2160
attcattaag cattctgccg acatggaagc catcacaaac ggcatgatga acctgaatcg    2220
ccagcggcat cagcaccttg tcgccttgcg tataatattt gcccatggtg aaaacggggg    2280
cgaagaagtt gtccatattg ccacgtttta aatcaaaact ggtgaaactc acccagggat    2340
tggctgagac gaaaaacata ttctcaataa acccttaggg aaataggcc aggttttcac     2400
cgtaacacgc cacatcttgc gaatatatgt gtagaaactg ccggaaatcg tcgtggtatt    2460
cactccagag cgatgaaaac gtttcagttt gctcatggaa aacggtgtaa caagggtgaa    2520
cactatccca tatccagcc tcaccgtctt tcattgccat acggaattcc ggatgagcat     2580
tcatcaggcg ggcaagaatg tgaataaagg ccggataaaa cttgtgctta tttttcttta    2640
cggtctttaa aaaggccgta atatccagct gaacggtctg gttataggta cattgagcaa    2700
ctgactgaaa tgcctcaaaa tgttctttac gatgccattg ggatatatca acggtggtat    2760
atccagtgat tttttttctcc attttagctt ccttagctcc tgaaaatctc gataactcaa    2820
aaaatacgcc cggtagtgat cttatttcat tatggtgaaa gttggaacct cttacgtgcc    2880
gatcaacgtc tcattttcgc caaaagttgg cccagggctt cccggtatca cagggacac     2940
caggatttat ttattctgcg aagtgatctt ccgtcacagg tatttattcg aagacgaaag    3000
ggcctcgtga tacgcctatt tttataggtt aatgtcatga taataatggt ttcttagacg    3060
tcaggtggca cttttcgggg aaatgtgcgc ggaaccccta tttgtttatt tttctaaata    3120
cattcaaata tgtatccgct catgagacaa taaccctgat aaatgcttca ataatattga    3180
aaaaggaaga gtatgagtat tcaacatttc cgtgtcgccc ttattccctt ttttgcggca    3240
ttttgccttc ctgttttgc tcacccagaa acgctggtga aagtaaaaga tgctgaagat     3300
cagttgggtg cacgagtggg ttacatcgaa ctggatctca acagcggtaa gatccttgag    3360
agttttcgcc ccgaagaacg ttttccaatg atgagcactt ttaaagttct gctatgtggc    3420
gcggtattat cccgtgttga tccccacagc aagatgcaac tttcgccaga tacgacggcg    3480
ctctttgccg tgctttctga cttttccattc gccttcacca agaccttca gcccggtgga    3540
atcaatcacc aggtgtgcga tttcaccccg ggtggacgtt ttgaaactga cattaaccga    3600
ctttgcccgc ttactgacac tggtgtaatc cgggcagcgc aacgaacgt tcatcagggc     3660
aaaaatggaa tcaataaaac cctgcgcagc ccgcagggtc agccggaata cgcgtttaat    3720
caccagaacg gtggtgatgg cgagatcaga atagcgctgg ggccttcctc gtgatgaagg    3780
```

```
tgttgccgac tcataccagg cctgaatcgc ctcatcatcc agccagaaag tgagggagcc   3840
acggttgatg agagctttgt tgtaggtgga ccagttggtg attctgaact tttgctttgc   3900
cacggaatgg tctgtgttgt cgggaggatg cgtgatctga tccttcaact cagcaaaagt   3960
tcgatttatt caacaaagcc actttcagta tggatttggg tgttacgggg ggggttggt    4020 gcttaaaatc gcgctgagga tttctgatgg tgttaagcgg gcggttttga gatgtaaact   4080
cgcccgttta acataatgga tcttgcgcgc accgcccgaa caccactcgc cacaaaaaac   4140
cgccggaacg tccaaaagta cgggttttgc tgcccgcaaa cgggctgttc tggtgttgct   4200
agtttgttat cagaatcgca gatccggctt cagccggttt gccggctgaa agcgctattt   4260
cttccagaat tgccatgatt ttttccccac gggaggcgtc actggctccc gtgttgtcgg   4320
cagctttgat tcgataagca gcatcgcctg tttcaggctg tctatgtgtg actgttgagc   4380
tgtaacaagt tgtctcaggt gttcaatttc atgttctagt tgctttgttt tactggtttc   4440
acctgttcta ttaggtgtta catgctgttc atctgttaca ttgtcgatct gttcatggtg   4500
aacagcttta aatgcaccaa aaactcgtaa aagctctgat gtatctatct tttttacacc   4560
gttttcatct gtgcatatgg acagttttcc ctttgatatg taacggtgaa cagttgttct   4620
acttttgttt gttagtcttg atgcttcact gatagataca agagccataa gaaccctcaga  4680 tccttccgta tttagccagt atgttctcta gtgtggttcg ttgttttttgc gtgagccatg   4740 agaacgaacc attgagatca tacttacttt gcatgtcact caaaaatttt gcctcaaaac   4800
tggtgagctg aattttttgca gttaaagcat cgtgtagtgt ttttcttagt ccgttatgta   4860
ggtaggaatc tgatgtaatg gttgttggta ttttgtcacc attcattttt atctggttgt   4920
tctcaagttc ggttacgaga tccatttgtc tatctagttc aacttggaaa atcaacgtat   4980
cagtcgggcg gcctcgctta tcaaccacca atttcatatt gctgtaagtg tttaaatctt   5040
tacttattgg tttcaaaacc cattggttaa gccttttaaa ctcatggtag ttattttcaa   5100
gcattaacat gaacttaaat tcatcaaggc taatctctat atttgccttg tgagttttct   5160
tttgtgttag ttcttttaat aaccactcat aaatcctcat agagtatttg ttttcaaaag   5220
acttaacatg ttccagatta tattttatga atttttttaa ctggaaaaga taaggcaata   5280
tctcttcact aaaaactaat tctaattttt cgcttgagaa cttggcatag tttgtccact   5340
ggaaaatctc aaagcccttta accaaaggat tcctgatttc cacagttctc gtcatcagct   5400
ctctggttgc tttagctaat acaccataag catttttccct actgatgttc atcatctgaa   5460
cgtattggtt ataagtgaac gataccgtcc gttctttcct tgtagggttt tcaatcgtgg   5520
ggttgagtag tgccacacag cataaaatta gcttggtttc atgctccgtt aagtcatagc   5580
gactaatcgc tagttcattt gctttgaaaa caactaattc agacatacat ctcaattggt   5640
ctaggtgatt ttaatcacta taccaattga gatgggctag tcaatgataa ttactagtcc   5700
tttttccttg agttgtgggt atctgtaaat tctgctagac ctttgctgga aaacttgtaa   5760
attctgctag accctctgta aattccgcta gacctttgtg tgttttttttt gtttatattc   5820 aagtggttat aatttataga ataaagaaag aataaaaaaa gataaaaaga atagatccca   5880
gccctgtgta taactcacta ctttagtcag ttccgcagta ttacaaaagg atgtcgcaaa   5940
cgctgtttgc tcctctacaa aacagacctt aaaaccctaa aggcttaagt agcaccctcg   6000
caagctcggg caaatcgctg aatattcctt ttgtctccga ccatcaggca cctgagtcgc   6060 tgtcttttc gtgacattca gttcgctgcg ctcacggctc tggcagtgaa tgggggtaaa    6120
tggcactaca ggcgcctttt atggattcat gcaaggaaac tacccataat acaagaaaag   6180
```

```
cccgtcacgg gcttctcagg gcgttttatg gcgggtctgc tatgtggtgc tatctgactt    6240
tttgctgttc agcagttcct gccctctgat tttccagtct gaccacttcg gattatcccg    6300
tgacaggtca ttcagactgg ctaatgcacc cagtaaggca gcggtatcat caacaggctt    6360
acccgtctta ctgtcgggga tc                                             6382

<210> SEQ ID NO 50
<211> LENGTH: 3872
<212> TYPE: DNA
<213> ORGANISM: Artificial Sequence
<220> FEATURE:
<223> OTHER INFORMATION: synthetic construct

<400> SEQUENCE: 50
aagcttggta cgttcgtgaa cacttcttcg gtaaatatcc tgaaaccgca gcactggttg      60
cagactggac tgacgagcag atctgggcac tgaaccgtgg tggtcacgat ccgaagaaaa     120
tctacgctgc attcaagaaa gcgcaggaaa ccaaaggcaa agcgacagta atccttgctc     180
ataccattaa aggttacggc atgggcgacg cggctgaagg taaaaacatc gcgcaccagg     240
ttaagaaaat gaacatggac ggtgtgcgtc atatccgcga ccgtttcaat gtgccggtgt     300
ctgatgcaga tatcgaaaaa ctgccgtaca tcaccttccc ggaaggttct gaagagcata     360
cctatctgca cgctcagcgt cagaaactgc acggttatct gccaagccgt cagccgaact     420
tcaccgagaa gcttgagctg ccgagcctgc aagacttcgg cgcgctgttg aagagcaga     480 gcaaagagat ctctaccact atcgctttcg ttcgtgctct gaacgtgatg ctgaagaaca     540
agtcgatcaa agatcgtctg gtaccgatca tcgccgacga agcgcgtact ttcggtatgg     600
aaggtctgtt ccgtcagatt ggtatttaca gcccgaacgg tcagcagtac accccgcagg     660
accgcgagca ggttgcttac tataaagaag acgagaaagg tcagattctg caggaaggga     720
tcaacgagct gggcgcaggt tgttcctggc tggcagcggc gacctcttac agcaccaaca     780
atctgccgat gatcccgttc tacatctatt actcgatgtt cggcttccag cgtattggcg     840
atctgtgctg ggcggctggc gaccagcaag cgcgtggctt cctgatcggc ggtacttccg     900
gtcgtaccac cctgaacggc gaaggtctgc agcacgaaga tggtcacagc cacattcagt     960
cgctgactat cccgaactgt atctcttacg acccggctta cgcttacgaa gttgctgtca    1020
tcatgcatga cggtctggag cgtatgtacg gtgaaaaaca agagaacgtt tactactaca    1080
tcactacgct gaacgaaaac taccacatgc cggcaatgcc ggaaggtgct gaggaaggta    1140
tccgtaaagg tatctacaaa ctcgaaacta ttgaaggtag caaaggtaaa gttcagctgc    1200
tcggctccgg ttctatcctg cgtcacgtcc gtgaagcagc tgagatcctg gcgaaagatt    1260
acggcgtagg ttctgacgtt tatagcgtga cctccttcac cgagctggcg cgtgatggtc    1320
aggattgtga acgctggaac atgctgcacc cgctggaaac tccgcgcgtt ccgtatatcg    1380
ctcaggtgat gaacgacgct ccggcagtgg catctaccga ctatatgaaa ctgttcgctg    1440
agcaggtccg tacttacgta ccggctgacg actaccgcgt actgggtact gatggcttcg    1500
gtcgttccga cagccgtgag aacctgcgtc accacttcga agttgatgct tcttatgtcg    1560
tggttgcggc gctgggcgaa ctggctaaac gtggcgaaat cgataagaaa gtggttgctg    1620
acgcaatcgc caaattcaac atcgatgcag ataaagttaa cccgcgtctg cgtcgagct    1680 cgaacaacaa caacaataac aataacaaca acctccagtc gacgacaaat cctggtgtat    1740
ccgcttggca ggtcaacaca gcttatactg cgggacaatt ggtcacatat aacggcaaga    1800
cgtataaatg tttgcagccc cacacctcct tggcaggatg ggaaccatcc aacgttcctg    1860
```

```
ccttgtggca gcttcaataa gaggtaaaag aataatggct atcgaaatca aagtaccgga    1920
catcggggct gatgaagttg aaatcaccga gatcctggtc aaagtgggcg acaaagttga    1980
agccgaacag tcgctgatca ccgtagaagg cgacaaagcc tctatggaag ttccgtctcc    2040
gcaggcgggt atcgttaaag agatcaaagt ctctgttggc gataaaaccc agaccggcgc    2100
actgattatg attttcgatt ccgccgacgg tgcagcagac gctgcacctg ctcaggcaga    2160
agagaagaaa gaagcagctc cggcagcagc accagcggct gcggcggcaa aagacgttaa    2220
cgttccggat atcggcagcg acgaagttga agtgaccgaa atcctggtga aagttggcga    2280
taaagttgaa gctgaacagt cgctgatcac cgtagaaggc gacaaggctt ctatggaagt    2340
tccggctccg tttgctggca ccgtgaaaga gatcaaagtg aacgtgggtg acaaagtgtc    2400
taccggctcg ctgattatgg tcttcgaagt gcgcgggtga agcaggcgcg gcagctccgg    2460
cgctaaacag gaagcagctc cggcagcggc ccctgcacca gcggctggcg tgaaagaagt    2520
taacgttccg gatatcggcg gtgacgaagt tgaagtgact gaagtgatgg tgaaagtggg    2580
cgacaaagtt gccgctgaac agtcactgat caccgtagaa ggcgacaaag cttctatgga    2640
agttccggcg ccgtttgcag gcgtcgtgaa ggaactgaaa gtcaacgttg gcgataaagt    2700
gaaaactggc tcgctgatta tgatcttcga agttgaaggc gcagcgcctg cggcagctcc    2760
tgcgaaacag gaagcggcag cgccggcacc ggcagcaaaa gctgaagccc cggcagcagc    2820
accagctgcg aaagcggaag gcaaatctga atttgctgaa aacgacgctt atgttcacgc    2880
gactccgctg atccgccgtc tggcacgcga gtttggtgtt aaccttgcga agtgaagggg    2940
cactggccgt aaaggtcgta tcctgcgcga agacgttcag gcttacgtga agaagctat    3000 caaacgtgca gaagcagctc cggcagcgac tggcggtggt atccctggca tgctgccgtg    3060
gccgaaggtg gacttcagca gtttggtga atcgaagaa gtggaactgg ccgcatcca    3120 gaaaatctct ggtgcgaacc tgagccgtaa ctgggtaatg atcccgcatg ttactcactt    3180
cgacaaaacc gatatcaccg agttggaagc gttccgtaaa cagcagaacg aagaagcggc    3240
gaaacgtaag ctggatgtga agatcacccc ggttgtcttc atcatgaaag ccgttgctgc    3300
agctcttgag cagatgcctc gcttcaatag ttcgctgtcg gaagacggtc agcgtctgac    3360
cctgaagaaa tacatcaaca tcggtgtggc ggtggatacc ccgaacggtc tggttgttcc    3420
ggtattcaaa gacgtcaaca gaaaaggcat catcgagctg tctcgcgagc tgatgactat    3480
ttctaagaaa gcgcgtgacg gtaagctgac tgcgggcgaa atgcagggcg gttgcttcac    3540
catctccagc atcggcggcc tgggtactac ccacttcgcg ccgattgtga acgcgccgga    3600
agtggctatc ctcggcgttt ccaagtccgc gatggagccg gtgtggaatg gtaaagagtt    3660
cgtgccgcgt ctgatgctgc cgatttctct ctccttcgac accgcgtga tcgacggtgc    3720 tgatggtgcc cgtttcatta ccatcattaa caacacgctg tctgacattc gccgtctggt    3780
gatgtaagta aaagagccgg cccaacggcc ggcttttttc tggtaatctc atgaatgtat    3840
tgaggttatt agcgaataga caaagcggcc gc    3872
```

<210> SEQ ID NO 51
<211> LENGTH: 2901
<212> TYPE: DNA
<213> ORGANISM: Artificial Sequence
<220> FEATURE:
<223> OTHER INFORMATION: synthetic construct

<400> SEQUENCE: 51

```
aagcttactc ggtgaatata tcggcaggat ctacaccgat gtccgcgccc gccccccgcta    60
ttttgttcag caagttatcc gtccatccag caaggaaaat gaataatgaa aaccgtcgtt   120
tttgcctacc acgatatggg atgcctcggt attgaagccc tgctggctgc cggttacgaa   180
attagcgcca tttttaccca tactgataat cccggtgaaa aagcctttta tggttcggtg   240
gctcgtctgg cggcggaaag aggcattccg gtttatgcgc cggataacgt taatcatccg   300
ctgtgggtgg aacgcattgc ccaactgtcg ccagatgtga ttttctcttt ttattatcgc   360
catcttattt acgacgaaat tttgcagctc gctcccgcag gtgcatttaa tctgcatggt   420
tcgctgttac caaaatatcg tggtcgcgcg ccgctgaact gggtgctggt caacggtgaa   480
acggaaactg gcgttacatt gcaccgaatg gtgaaacgtg ccgatgccgg ggccattgtg   540
gcgcaactgc gcattgccat tgcgccagac gatatcgcta ttacgctgca tcataaattg   600
tgccatgccg cgcgccagct actggaacag acattacccg ccattaaaca cggtaatatt   660
ctggaaatcg cccagcgcga aaacgaagcc acctgttttg tcgcagaaac gccggatgac   720
agtttccttg aatggcataa accggcatcg gtactgcaca acatggtacg tgccgttgcc   780
gatccgtggc cgggtgcctt cagctatgtt ggcaatcaga aattcaccgt ctggtcgtcg   840
cgtgttcatc ctcatgccag caaagcacag ccggggagcg tgatttctgt tgcgccactg   900
ctgattgcct gtggcgatgg cgcgctggaa atcgtcaccg gacaggcggg cgacggcatt   960
actatgcagg gctcgcaatt agcgcagacg ctgggcctgg tgcaaggttc acgcttgaat  1020
agccagcctg cctgcaccgc ccgacgccgt acccgggtac tcatcctcgg ggtgaatggc  1080
tttattggca accatctgac agaacgcctg ctgcgcgaag atcattatga agtttacggt  1140
ctggatattg gcagcgatgc gataagccgt tttctgaatc atccgcattt tcactttgtt  1200
gaaggcgata tcagtattca ttccgaatgg attgagtatc atgtcaaaaa atgtgatgtc  1260
gtcttgccgc tggtgcgat agccacgccg attgaatata cccgcaaccc gctgcgcgta  1320
tttgaactcg attttgaaga gaatctgcgc attatccgct actgcgtgaa gtaccgtaag  1380
cgaatcatct tcccgtcaac ttcagaagtt tatgggatgt gtagcgataa atacttcgat  1440
gaggaccatt ctaatttaat cgtcggcccg gtgaataaac cacgctggat ttattcggta  1500
tcaaaacaat tacttgatcg ggtgatctgg gcctatggcg aaaagagggg tttacagttc  1560
accctcttcc gcccgtttaa ctggatggga ccacgactgg ataaccttaa tgcagcgcga  1620
attggcagct cccgcgctat tacgcaactc attctcaatc tggtagaagg ttcaccgatt  1680
aagctgattg atggcggaaa acaaaaacgc tgctttactg atattcgcga tggtatcgag  1740
gcgttatacc gcattatcga aaatgcggga aatcgctgcg acggtgaaat tatcaacatt  1800
ggcaatcctg agaacgaagc gagcattgag gaactgggcg agatgctgct ggcgagcttc  1860
gaaaaacatc cgctgcgcca tcatttccca ccgtttgcgg gctttcgcgt tgtcgaaagt  1920
agcagctact acggcaaagg atatcaggac gtagagcatc gtaaaccgag catccgcaat  1980
gcccaccgct gcctggactg ggagccgaaa attgatatgc aggaaaccat cgacgaaacg  2040
ctggatttct tcctgcgcac cgttgatctt acggataaac cttccctgca ggcttcgagc  2100
tcgaacaaca acaacaataa caataacaac aacctccagt cgacgacaaa tcctggtgta  2160
tccgcttggc aggtcaacac agcttatact gcgggacaat tggtcacata taacggcaag  2220
acgtataaat gtttgcagcc ccacacctcc ttggcaggat gggaaccatc caacgttcct  2280
gccttgtggc agcttcaaga taaaccatca tgaccaaagt aggcttacgc attgatgtcg  2340
```

| | |
|---|---|
| ataccttccg tggcacccgt gaaggcgtgc cgcgtctgct ggaaatcttg agtaagcata | 2400 |
| atattcaggc cagcattttt ttcagcgtcg gcccggacaa tatgggccgc catctctggc | 2460 |
| actggtgaag ccacagtttt tgtggaagat gctgcgctca aacgcggcat cgctttatgg | 2520 |
| ctgggatatt ttactggcag gtacggcctg gccaggtaaa gagattggtc atgccaatgc | 2580 |
| cgatatcatt cgtgaagcgg ctaaacatca cgaagtcggc ctgcacgcct gggatcacca | 2640 |
| tgcctggcaa gcccgtagcg gtaactggga tcggcaaaca atgatcgacg atattgcacg | 2700 |
| cggtcttcgc actctggaag agattatcgg tcaaccggta acctgttctg ccgctgcggg | 2760 |
| ctggcgtgcc gaccagaagg tgatcgaagc aaaagaagcg ttccatttgc gctacaacag | 2820 |
| cgattgtcgt ggggccatgc cgttccgtcc attgctcgaa tcaggaaacc ctggcactgc | 2880 |
| gcaaattccg gtgacggtac c | 2901 |

<210> SEQ ID NO 52
<211> LENGTH: 1794
<212> TYPE: DNA
<213> ORGANISM: Artificial Sequence
<220> FEATURE:
<223> OTHER INFORMATION: synthetic construct

<400> SEQUENCE: 52

| | |
|---|---|
| aagcttcgag atcgtaacca aatacgctga cccgcccgga ggttttattt accagagagc | 60 |
| tgataatacc gatagtgtcg atttcccggc cccgttcggc ccgagaagcg cataaaaatc | 120 |
| acccgcttcg acctgcaaat ctatcccacg aagcgcctga cgccgcctg dataggtttt | 180 |
| tttaagctgt tgaagttcca gtgcaatggt cataaatttt tacttacctt acgttcttac | 240 |
| actttatctg tggtttaaat cgtcccggag ttgccctata ttagccaaac gtaattattt | 300 |
| ggttacaggt cgttaacctc catgaaagac atagatacac tcatcagcaa caatgcacta | 360 |
| tggtcaaaaa tgctggtgga agaggatccc gggttttttg agaaactggc acaagcgcaa | 420 |
| aaaccgcgct ttctatggat tggatgttcc gacagtcgcg ttcctgcaga acgtttaacc | 480 |
| ggtcttgagc cgggcgaact cttttgttca cgtaatgttg ctaacctggt cattcacact | 540 |
| gacctgaact gccttttccgt ggttcagtat gcagtggatg tactcgaagt tgaacacatt | 600 |
| attatctgtg ccactacgg ttgcggcggc gtacaagccg cagttgaaaa cccggaactg | 660 |
| gggcttatca caactggct gctgcatatc cgcgatatct ggttcaaaca tagctcattg | 720 |
| ctcggcgaaa tgccgcaaga gcgccgtctg ataccttgt gtgaactgaa cgtcatggaa | 780 |
| caggtgtata acctgggcca ctccaccatt atgcaatcag cgtggaaacg cgggcagaaa | 840 |
| gttaccattc acgctgggc ctacggcatt cacgacggct tgctgcgtga tctggatgtt | 900 |
| accgccacca accgcgaaac ccttgagcaa cgttaccgtc acgggatttc caacctcaag | 960 |
| ctgaaacacg ccaaccacaa atcgagctcg aacaacaaca acaataacaa taacaacaac | 1020 |
| ctccagtcga cgacaaatcc tggtgtatcc gcttggcagg tcaacacagc ttatactgcg | 1080 |
| ggacaattgg tcacatataa cggcaagacg tataaatgtt tgcagcccca cacctccttg | 1140 |
| gcaggatggg aaccatccaa cgttcctgcc ttgtggcagc ttcaataagc gatcgcaaat | 1200 |
| gccatgccga atgcaacaca tccggcaact tcacacttac tcgtccagca gaatcacttt | 1260 |
| gccgatatac ggcagatgac ggtaacgctg tgcgtaatca atgccgtaac ccaccacaaa | 1320 |
| ctcatccggg atcgagaaac cgataaattc taccggacg ttcacttcac gacgggacgg | 1380 |
| tttatccagc agcgtacaaa tcgccagcga cttcggttcg cgcaggctta agatctcacg | 1440 |
| cactttcgac agtgtattcc ccgagtcgat gatatcttca acaatcagca cgtccttgcc | 1500 |

| | |
|---|---|
| acggatatct tcatccagat ctttgaggat tttcacatca cgggtggtgg acatgccgct | 1560 |
| accgtagctg gaggcggtca taaagtcgac ttcatgagat acctgaactt cacggcacag | 1620 |
| gtccgccata aacataaatg agccacgcag cagacccacc agcaccatat cgctgccgct | 1680 |
| gtctttgtaa cgctcagtaa tctgacgacc cagttcggcg atacgcgctt taatctccgc | 1740 |
| ttcggggatc attacttcta cagtatgttt catatctcta accatatgcg gccg | 1794 |

<210> SEQ ID NO 53
<211> LENGTH: 1588
<212> TYPE: DNA
<213> ORGANISM: Artificial Sequence
<220> FEATURE:
<223> OTHER INFORMATION: synthetic construct

<400> SEQUENCE: 53

| | |
|---|---|
| aagcttgtta agtgcggaca tcagatgcga gaagcagaca aagaagcccg cgatcacgtt | 60 |
| cgcaaagatg agcaagtgat cgggattttt catccggact agcgatatgc gccgagtttt | 120 |
| tttaagctag tgagtacacg gctgcagaat tccgctacaa tctgcgccac tattcttccc | 180 |
| atgctcagga gatatcatga agtagcaaa agacctggtg gtcagcctgg cctatcaggt | 240 |
| acgtacagaa gacggtgtgt tggttgatga gtctccggtg agtgcgccgc tggactacct | 300 |
| gcatggtcac ggttccctga tctctggcct ggaaacggcg ctggaaggtc atgaagttgg | 360 |
| cgacaaattt gatgtcgctg ttggcgcgaa cgacgcttac ggtcagtacg acgaaaacct | 420 |
| ggtgcaacgt gttcctaaag acgtatttat gggcgttgat gaactgcagg taggtatgcg | 480 |
| tttcctggct gaaaccgacc agggtccggt accggttgaa atcactgcgg ttgaagacga | 540 |
| tcacgtcgtg gttgatggta accacatgct ggccggtcag aacctgaaat tcaacgttga | 600 |
| agttgtggcg attcgcgaag cgactgaaga agaactggct catggtcacg ttcacggcgc | 660 |
| gcacgatcac caccacgatc acgaccacga cggttgctgc ggcggtcatg ccacgatca | 720 |
| cggtcatgaa cacggtggcg aaggctgctg tggcggtaaa ggcaacggcg gttgcggttg | 780 |
| ccacctgcag gcttcgagct cgaacaacaa caacaataac aataacaaca acctccagtc | 840 |
| gacgacaaat cctggtgtat ccgcttggca ggtcaacaca gcttatactg cgggacaatt | 900 |
| ggtcacatat aacggcaaga cgtataaatg tttgcagccc cacacctcct ggcaggatg | 960 |
| ggaaccatcc aacgttcctg ccttgtggca gcttcaataa gcgatcgcat accgaaaaag | 1020 |
| tgacaaaaaa gcggggaatc cccgcttttt ttacgcctca ataatgtggc ggtggcgttt | 1080 |
| cttcagcctg cgacgcgatg ttcgacggct ggctggcttt taacttctcg gtcagcagac | 1140 |
| gcagatgatc gcgcagtttc gccatctcca tttcatgagc ggtcaccgtg acgttcagtt | 1200 |
| cttcaatggt gatttcctga aaagccagtc ggctctccag ctctgccagg cgtgcttcca | 1260 |
| atgataaatc ctgcatgatt cacctctttt gtcgaatggt cgccgcggat tctacttaac | 1320 |
| tttgctgccc gagacagcac tcatttcgcg gtcatcgaaa ctaatttaaa caaaaagagt | 1380 |
| ctgaaaatag atgataatag ggcgtgtctg tatgtagatt tgttcgacaa cgctttatag | 1440 |
| taccottctg ataatagtta accctggggt gagatgcccc gatcctggag atatggatga | 1500 |
| aatcactgtt taaagtaacg ctgctggcga ccacaatggc cgttgccctg catgcaccaa | 1560 |
| tcactttttgc tgctgaagct gccggccg | 1588 |

US 8,981,067 B2

COMPOSITION, METHOD AND KIT FOR OBTAINING PURIFIED RECOMBINANT PROTEINS

CROSS REFERENCE

This application is a §371 application of international application number PCT/US2011/049356 filed on Aug. 26, 2011, which claims priority from U.S. provisional application No. 61/381,736 filed Sep. 10, 2010, herein incorporated by reference.

BACKGROUND OF THE INVENTION

Production of proteins of interest is commonly achieved in transformed competent host cells. A problem that arises during purification of such proteins is that contaminant host proteins co-purify with the protein of interest. One approach to tackling this problem is to form a fusion protein between the protein of interest and a protein tag that has an affinity to a matrix. It is intended that the contaminant proteins are washed away and a pure protein is recovered. An example of a protein tag that is widely used is a histidine tag (His-tag). This binds to a metal containing column. The method is called immobilized metal ion affinity chromatography (see for example U.S. Pat. No. 5,310,663).

Unfortunately, contaminating host cell proteins which do not carry any form of tag may contain non-consecutive histidine residues or other metal binding motifs exposed to the surface of their ternary structure. These contaminating proteins also bind to nickel and/or cobalt containing purification resins to which the His-tagged protein of interest binds (see Bolanos-Garcia and Davies, *BBA* 1760: 1304-1313(2006), and Edwards, et al., *Nature Methods* 5: 135-146(2008)), resulting in co-purification of these contaminants and failure to obtain a purified preparation of the protein of interest.

SUMMARY OF THE INVENTION

Embodiments of the invention provide a composition that includes a variant host cell derived from a parent host cell where the host cell may be a prokaryotic cell such as a bacterial cell such as *E. coli* or a eukaryotic cell. The parent host cell is characterized by a genome encoding a plurality of essential host proteins, wherein one or more essential proteins contain a plurality of histidines or basic amino acids residues such that when the cell is lysed, these essential proteins are capable of binding to a metal chelating matrix. Examples of such essential proteins include SlyD, carbonic anhydrase (can), ArnA, ArnD AceE, AceF and GlmS.

In one embodiment, the variant viable host cell differs from the parent host cell in that in the variant, at least one of the plurality of essential proteins is additionally fused to an affinity binding tag encoded by the genome, the fusion proteins being capable of binding to a non-metal affinity matrix. Examples of affinity binding tags include: an immunoaffinity tag, a peptide tag selected from hemagglutinin, c-myc, T7, Glu-Glu, GST-tag, ZZ, GB1, MCP, and ACP, a streptavidin binding tag or a chitin binding domain tag. Alternatively, at least one of the plurality of essential proteins is mutated such that at least two of the plurality of histidines or basic amino acid residues is replaced with non-histidine residues such as alanine so that the mutated essential protein is no longer able to bind the metal chelating matrix. The variant host cell is capable of being transformed to express a recombinant target protein.

The host cell variants may further include a non-host DNA encoding a protein of interest.

In an embodiment of the invention, a method is provided of isolating a recombinant target protein from a cell lysate, that includes (a) lysing variant host cells of the type described above, wherein the variant host cells are transformed with DNA encoding a target protein fused to a histidine-tag, (b) subjecting the lysed host cells to a metal chelating matrix and a non-metal affinity binding matrix where the metal chelating matrix and the non-metal affinity binding matrix may be contained in the same or different reaction vessels; and (c) isolating the recombinant protein from the cell lysate.

In another embodiment of the invention, a composition is provided which includes an affinity non-metal binding matrix and a metal chelating matrix proximately located in a reaction vessel suitable for receiving a mixture of components and suitable for separating a subset of the components from the mixture.

In another embodiment of the invention, a method is provided of isolating a recombinant protein from a cell lysate. The method includes: lysing variant host cells that express a recombinant protein fused to a His-tag and purifying the recombinant protein away from essential protein contaminants that have histidine residues or basic amino acids and are capable of binding to a metal chelating matrix. This is achieved either by fusing the DNA encoding one or more essential proteins to DNA encoding an affinity binding tag and substituting the essential protein in the host cell chromosome using homologous recombination; or mutating at least two histidines or basic amino acids in the essential protein contaminant so that the one or more essential proteins no longer bind to a metal chelating matrix. The lysed host cells are then exposed to at least one of a metal chelating matrix and a non-metal binding matrix; and the purified recombinant protein is obtained from the cell lysate.

BRIEF DESCRIPTION OF THE FIGURES

The following description and the accompanying figures further describe and exemplify the features and advantages of the present invention, where:

FIG. 2 shows the nucleotide sequence of the pMAKCBD allele exchange vector (SEQ ID No: 49).

Lanes 1 and 10 contains a 10-250 kDa protein ladder (New England Biolabs, Inc., Ipswich, Mass.).

Lane 11 is Ni-NTA column flow through.

Lanes 2-9 and 12-22 are imidazole elution fractions containing eluted His-tag proteins and metal binding contaminating proteins.

Arrows identify the target protein AlaRS(6His) (approx 90 kDa). The black box shows that native *E. coli* protein SlyD (approx. 26-28 kDa) is a metal binding contaminating protein and co-elutes with target AlaRS(6His) protein.

FIG. 3B: shows the results of gel electrophoresis of samples obtained by column fractionation of cell lysates of ER3135(slyD-CBD derivative) over-expressing a target protein AlaRS(6His). The column used here is an Ni-NTA column. In the absence of a chitin purification step, it was shown here that the co-eluting SlyD-CBD migrated at a position that was consistent with the presence of the CBD-tag on the SlyD.

Lanes 1 and 14 contains the 10-250 kDa protein ladder.

Lane 15 is HisTrap™ flow through.

Lanes 2-13 and 16-26 are imidazole elution fractions.

The arrows identify AlaRS(6His). SlyD-CBD migrates at 35-40 kDa and is highlighted by a dotted black box.

FIG. 3C shows results of a Western Blot in which anti-CBD antibody is applied to the gel in FIG. 3B confirming that the band on the gel at 35-40 kDa corresponds to SlyD-CBD contamination of the AlaRS(6His) in lanes 9-13 and 16-25 (see dotted black line box).

FIG. 4 shows removal of the CBD-tagged contaminants from the AlaRS(6His) (protein of interest) using a chitin column following a Ni-NTA chromatography step (QIA express manual, (Qiagen, Germantown, Md.)). Ni-NTA and chitin column fractions were analyzed by Western blotting using an anti-CBD antibody (New England Biolabs, Ipswich, Mass.) which reacts with any CBD in the fraction. The positions of bands corresponding to AceE-CBD; ArnA-CBD; SlyD-CBD; and Can-CBD are marked. The host strain used in this experiment is ER3203. The Ni-NTA fractions correspond to lanes identified as Ly, S, ft, W1, W2 and P The fractions obtained after affinity binding to a chitin column overnight are shown in lanes F, W, B, F, W B.

Lane L contains a biotinylated protein ladder (Cell Signaling Technology, Beverly, Mass.).

Lane Ly is a sonication lysate.

Lane S is a supernatant from the sonicated sample.

Lane ft is a flow-through from the Ni-NTA column.

Lane w1 contains the first wash of the Ni-NTA column.

Lane w2 contains the second wash of the Ni-NTA column.

Lane P contains the pooled fractions of Ni-NTA eluate which contain tagged protein without chitin column purification Lanes F contains a flow-through from chitin columns after 1 hr or 18 hrs of incubation.

Lanes W contains a wash of chitin columns after 1 hr or 18 hrs of incubation.

Lanes B contains the eluate obtained from boiling the chitin resin which had been incubated for 1 hr or 18 hrs.

Lane WC contains whole cell lysate from *E. coli* ER3203 encoding AceE-CBD, ArnA-CBD, SlyD-CBD, Can-CBD and over-expressing AlaRS(6His).

Figure 5:
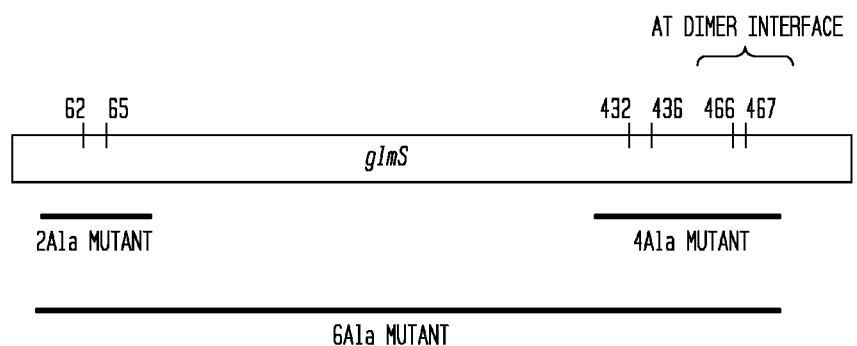

FIG. 5 shows positions of histidine (His) residues within the GlmS amino acid sequence which were mutated to alanine (Ala). Three mutants are shown: the GlmS(2Ala) mutant containing the mutations His62Ala and His65Ala, the GlmS (4Ala) mutant containing the mutations His432Ala, His436Ala, His466Ala and His467Ala, and the GlmS(6Ala) mutant containing all the mutations of the 2Ala and 4Ala mutants.

Figure 6:
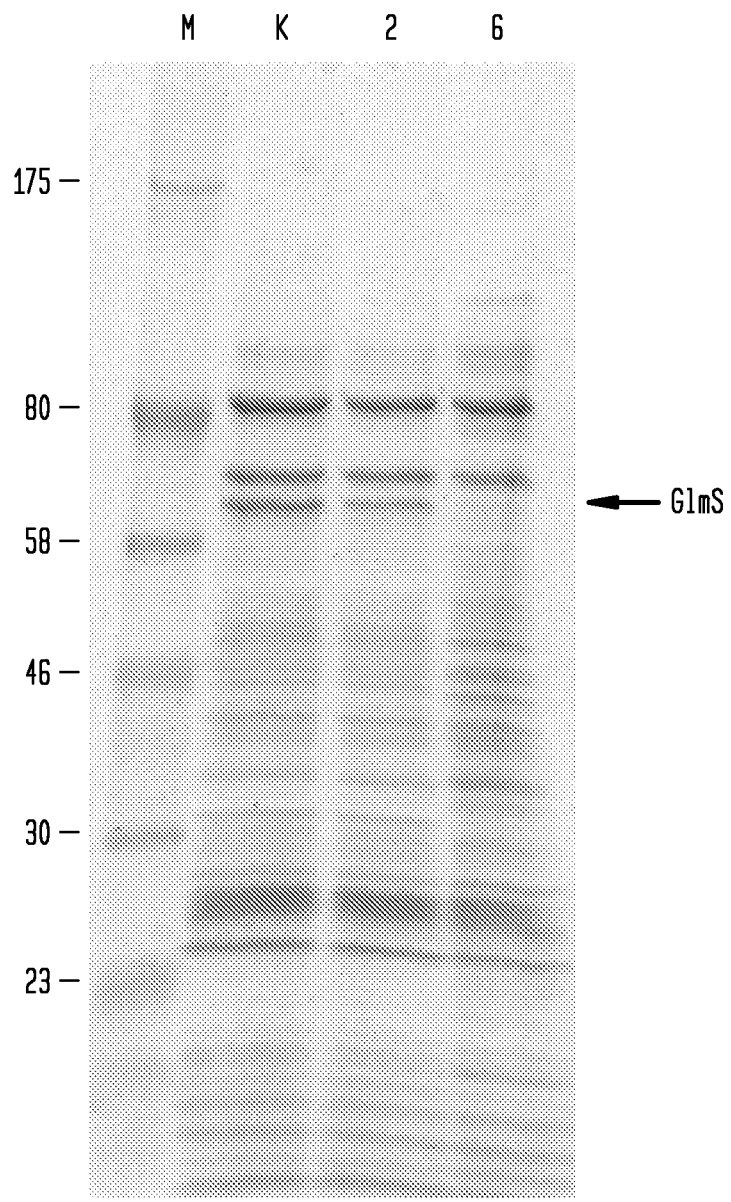

FIG. 6 shows the results of SDS-PAGE of the Ni-NTA column elution of cell extract proteins of *E. coli* ER3135 expressing WT GlmS, Glms(2Ala) or GlmS(6Ala) from the pMAK705 vector.

Lane (M) contains 7-175 kDa protein marker.

Lane (K) shows Ni-NTA binding proteins from ER3135 expressing WT
GlmS.

Lane (2) shows Ni-NTA binding proteins from ER3135 expressing the GlmS(2Ala).

Lane (6) shows Ni-NTA binding proteins from ER3135 expressing the GlmS(6Ala). An arrow indicates the expected position of GlmS (67 kDa) which is absent owing to the altered properties of GlmS(6Ala) that prevent it from binding.

Figure 7:
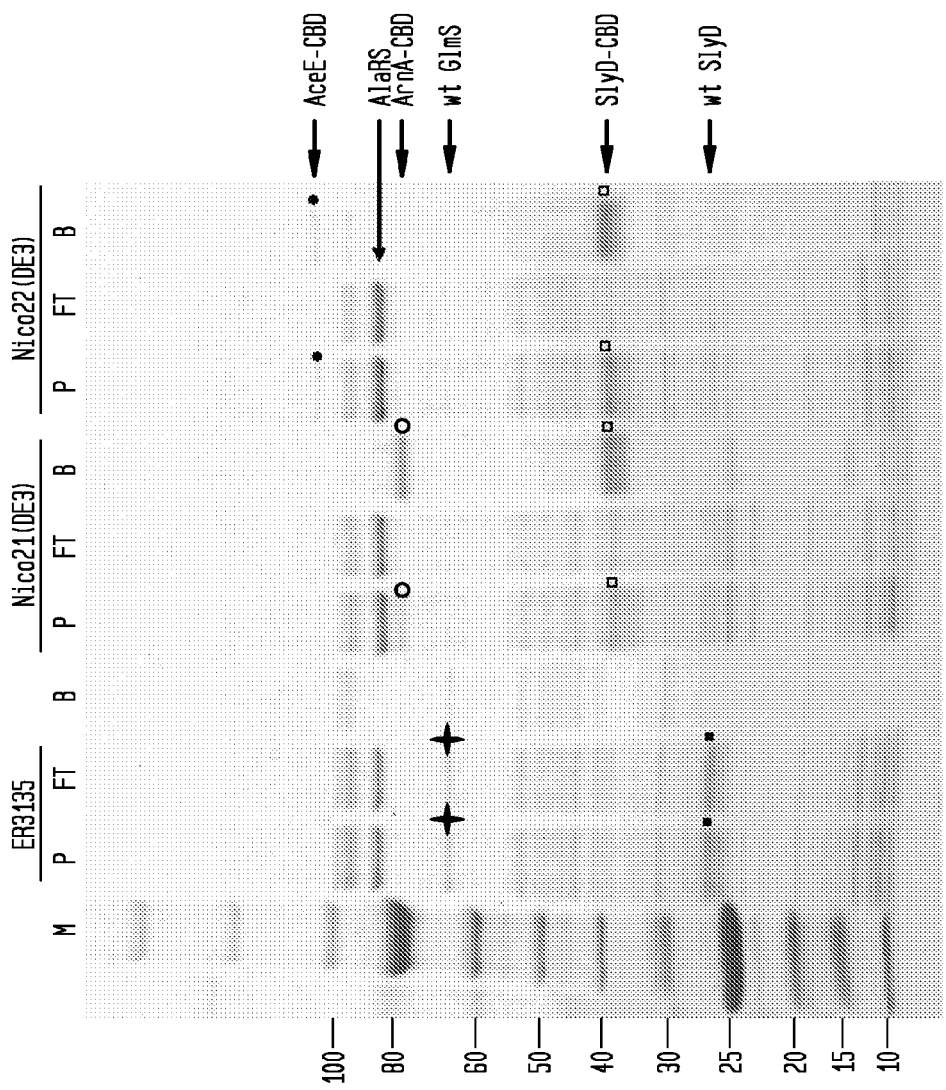

FIG. 7 shows SDS-PAGE results of over-expressing AlaRS (6His) in 3 strains—ER3135 which are wild type cells with no modification; Nico21(DE3) which contains three CBD-tagged non-target nickel binding proteins and GlmS(6Ala), and Nico22(DE3) which contains four CBD-tagged non-target nickel binding proteins and the GlmS(6Ala).

M=marker

P=pooled samples from Ni-NTA eluate enriched in AlaRS (6His) target protein

FT=flow through after exposing Ni-NTA eluate to chitin resin

B=eluate obtained from boiling the chitin resin to release bound CBD-tagged proteins Arrows identify AceE-CBD, AlaRS(6His), ArnA-CBD and SlyD-CBD. GlmS(6Ala) is not detected in Nico21(DE3) and Nico22(DE3) samples because the mutations eliminate binding to the Ni-NTA column. The position of WT GlmS is identified by a black triangle and WT SlyD is identified by black square in ER3135 pool (P) and flow through (FT).

FIG. 8A-D are DNA sequences cloned into pMAKCBD in order to perform chromosomal allele exchange.

FIG. 8A is a sequence of the aceE-CBD-aceF allele (SEQ ID NO: 50).

FIG. 8B is a sequence of the arnA-CBD-arnD allele (SEQ ID NO: 51).

FIG. 8C is a sequence of the can-CBD allele (SEQ ID NO: 52).

FIG. 8D is a sequence of the slyD-CBD allele (SEQ ID NO: 53).

Figure 9:
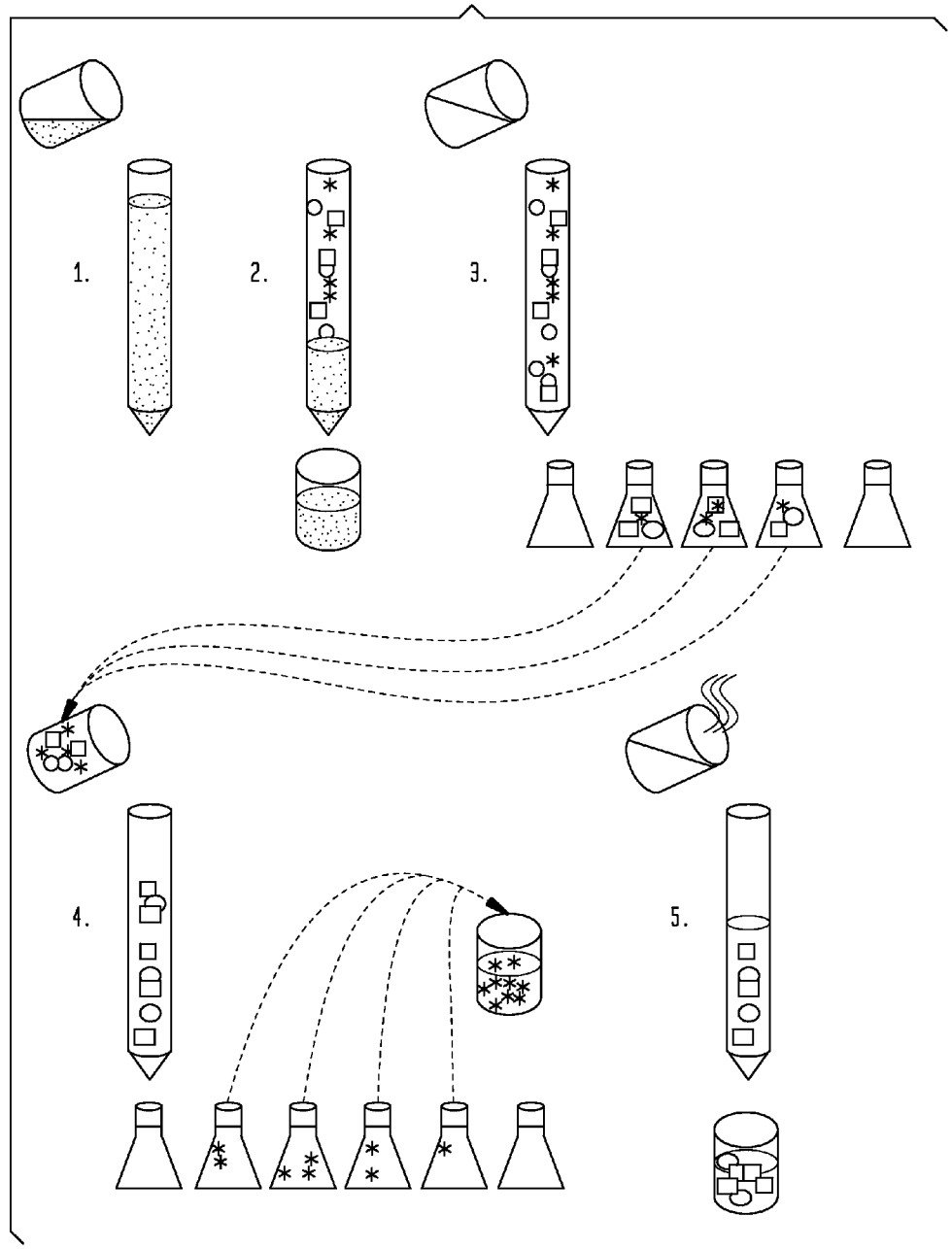

FIG. 9 shows a schematic of the process of using a metal chelating matrix and an affinity binding matrix to purify a protein of interest expressed in Nico cells.

1. Cell lysate in solution is applied to the metal chelate chromatography column.

2. The lysate is allowed to flow through the column. The His-tagged protein of interest (*) and the affinity-tagged contaminating proteins (white squares and circles) remain bound to the column after rinsing.

3. The bound proteins are eluted with buffer which weakens the binding of the proteins to the metal ion. Fractions are collected from the column and tested for the presence of the protein of interest. Fractions containing the protein of interest are pooled.

4. The pooled fractions are applied to a second chromatography column containing a matrix which specifically binds the affinity-tagged contaminating proteins. The flow-through containing the isolated protein of interest is retained.

5. The affinity-tagged contaminating proteins bound to the matrix may be eluted with a buffer which weakens the binding of the affinity-tag to the matrix. A particular example is illustrated here, in which a column containing a chitin matrix is treated with boiling water to release bound CBD-tagged proteins.

Figure 10:
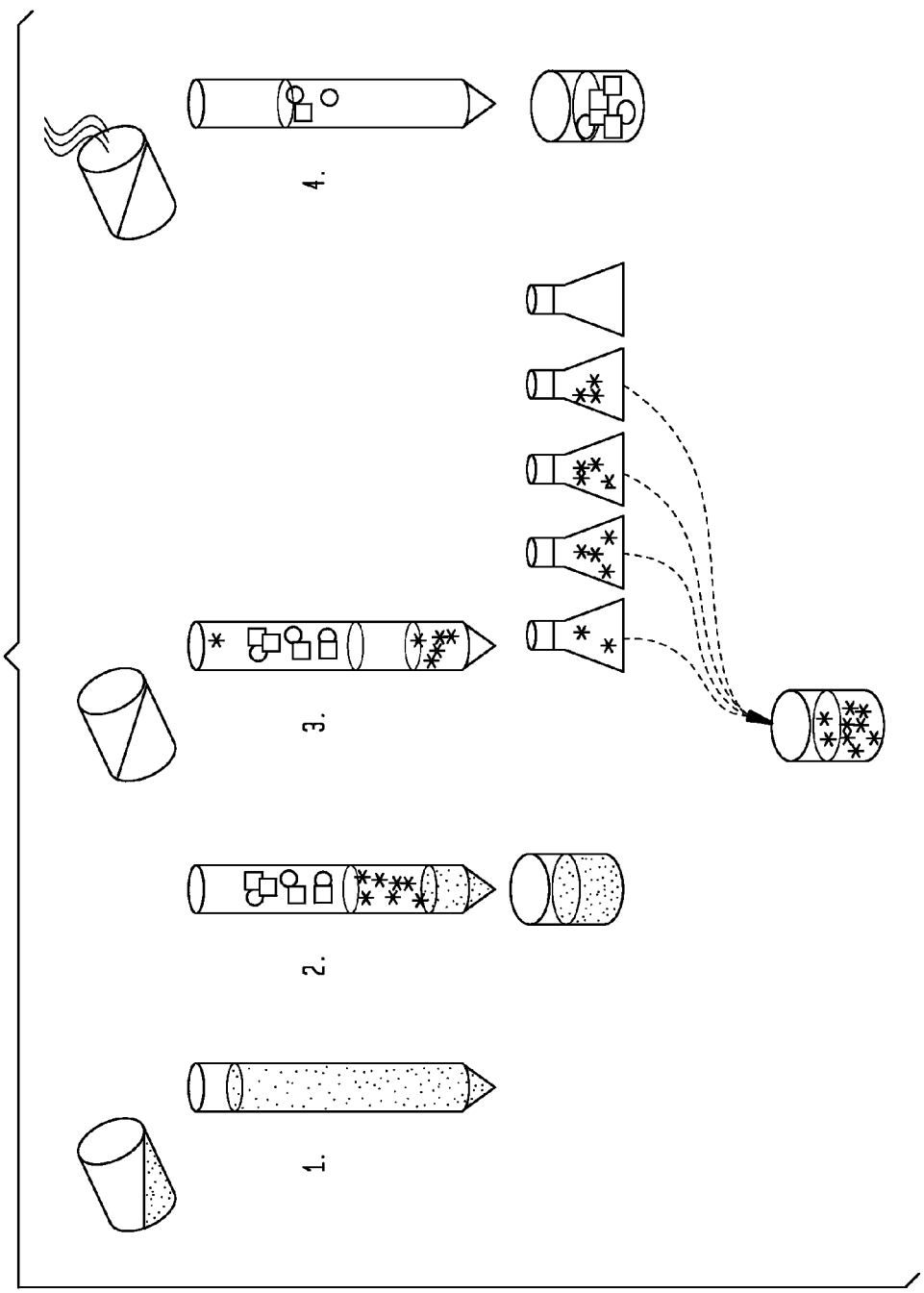

FIG. 10 shows a schematic of the process of using an affinity layer and a metal chelate layered column to purify a protein of interest expressed in Nico cells.

1. Cell lysate in solution is applied to a column containing distinct matrix layers, wherein the solution runs through a matrix layer which specifically binds affinity-tagged contaminating proteins ("affinity layer") before the solution runs through a metal chelating matrix ("metal chelate layer").

Note: the position of the layers may be reversed so that the cell lysate is exposed to the metal chelate layer before the affinity layer.

2. The lysate is allowed to flow through the column and then the column is rinsed. The affinity-tagged contaminating proteins (white squares and circles) bind to the affinity layer while the His-tagged proteins of interest flow through the affinity layer and are bound by the metal chelate layer.

3. The bound proteins of interest are eluted with buffer which weakens the binding of the metal-binding peptide tag to the metal chelate layer but does affect the binding of the affinity-tagged proteins for the affinity layer. Fractions are collected from the column and tested for the presence of the protein of interest. Fractions containing the isolated protein of interest are retained.

4. The affinity-tagged contaminating proteins bound to the matrix may be eluted with a buffer which weakens the binding of the affinity-tag to the matrix. A particular example is illustrated here, in which a column containing a chitin matrix is treated with boiling water to release bound CBD-tagged proteins.

DETAILED DESCRIPTION OF THE EMBODIMENTS

Embodiments of the invention provide solutions to the problem of co-purification of contaminating essential host cell proteins containing histidines with His-tagged proteins of interest so that His tagged proteins of interest may be readily isolated from essential host cell proteins containing histidine residues. ("His-tag" as used here refers to more than 2 consecutive His residues in a protein fusion tag (EP0282042; U.S. Pat. No. 5,284,933, U.S. Pat. No. 5,310,663) and includes protein fusion tags capable of metal binding where histidine residues are non-consecutive (see US 2006/0030007 and U.S. Pat. No. 7,176,298)). The methods described herein can be readily applied to non-essential host proteins also although it is a relatively easy matter to delete or mutate the host genes encoding the non-essential proteins.

In one embodiment, a desired expression strain was generated using an allele exchange vector containing a gene encoding a contaminating histidine-containing essential protein fused to an open reading frame (ORF) is encoding a protein affinity binding tag. The term "affinity binding tag" refers to a peptide or protein that is not a metal binding protein or peptide. Once transformed with the plasmid, the host cell could express a fusion protein that included an affinity binding protein fused to the contaminating essential host protein wherein the essential protein was active and the host cell viable. The fusion gene was inserted into the host cell chromosome at the native gene locus to replace the native gene by homologous recombination (For example, see Hamilton, et al., *Journal of Bacteriology*: 4617-4622 (1989)). In this way viability of the host cell was preserved by expression of an active affinity-tagged protein from the native gene locus and subsequent expression of the His-tagged protein of interest was possible.

The protein of interest could then be purified away from contaminating host metal binding proteins. In one embodiment, the crude cell lysate was first added to a metal chelating matrix which separates metal binding proteins from non-metal binding proteins resulting in a purified mixture of the protein of interest and contaminating histidine-containing fusion proteins. The fusion protein (affinity binding protein-contaminating essential host protein) was then removed by means of an affinity matrix from the target proteins.

In other embodiments of the method, the metal binding chelating matrix could be used after binding of the cell lysate to an affinity matrix or both matrices could be used at the same time for purifying the protein of interest. The purification may be performed in separate or the same reaction vessels.

Examples of *E. coli* host proteins that were reported to be co-eluted from IMAC resin in significant amounts were DnaK, GlmS, AceE, EF-Tu, ArnA, RNase E, AtpF, CRP, Can, the Rho transcription terminator and SlyD. The most consistent and significant contaminants are SlyD, GlmS, Can, ArnA and AceE. The examples show how genes expressing these proteins were targeted by modifying the host chromosome using homologous recombination. Using the same or similar approach, any desired protein additional to those in the examples can be similarly targeted and then removed from the preparation containing the protein of interest (target protein) by affinity-binding to a selected affinity matrix.

There are a wide range of affinity binding proteins or peptide-tags known in the art that are characterized by being capable of binding to an affinity matrix. Any of these may be utilized in embodiments of the invention. These include: immuno-affinity tags such as FLAG tag (DYKDDDDK) (SEQ ID NO: 1) that binds to ANTI-FLAG® M2 Affinity Gel (Sigma, St. Louis, Mo.); hemagglutinin (HA); c-myc, T7; Glu-Glu (which mediates protein binding to the respective immobilized antibody or ligand (Table 9.9.1 in *Current Protocols in Protein Science*, authors Michelle E. Kimple and John Sondek (2004)); StrepII Tag (WSHPQFEK) (SEQ ID NO: 2) (that binds to streptavidin and StrepTacti™ resin (GE Healthcare, Waukesha, Wis.)); and Biotin Carboxyl Carrier Protein (BCCP) (a natural substrate for BirA biotin ligase (Cronan, J. E., *J. Biol. Chem.* 265:10327-10333 (1990)). BCCP-tagged proteins are biotinylated in vivo in birA+expression hosts. The biotin group mediates protein binding to streptavidin and StrepTactin™ resin. AviTag™ (GeneCopoeia, Rockville, Md.) (GLNDIFEAQKIEWH) (SEQ ID NO: 3) may also be biotinylated by the BirA protein in vivo or in vitro (Beckett D., et al., Protein Science 8: 921-929 (1999)). This biotinylated peptide is capable of high affinity binding to streptavidin and StrepTactin™ resin. The S-Tag™ (EMD Biosciences, Darmstadt, Germany) binds to S-protein agarose. The GST-tag, ZZ-tag, GB1-tag are also suitable for contaminant protein tagging (F. Freuler, et al., *Protein Expression and Purification* 59: 232-241(2008)). YbbR-tags (J. Yin, et al., *PNAS* 102: 15815-15820 (2005)) may be specifically labeled with biotin by Sfp phosphopantetheinyl transferase for subsequent binding to streptavidin and StrepTactin™ resin. S6 and A1 peptides were identified from a phage-display library as efficient substrates for site-specific protein labeling catalyzed by Sfp and AcpS phosphopantetheinyl transferases (Zhou, Z., et al., *ACS Chem. Biol.* 2: 337-346 (2007)). Labeling with biotin-CoA allows for subsequent binding of the tagged protein to streptavidin and StrepTactin™ resin. The MCP-tag and ACP-tag (New England Biolabs, Inc., Ipswich, Mass.) may be labeled with derivatives of coenzyme A (e.g. biotin-CoA). In the labeling reaction, the substituted phosphopantetheine group of CoA is covalently attached to a conserved serine residue by SFP-Synthase or ACP-Synthase, respectively. CBD tag is small and binds chitin very tightly. In the examples described herein, the chitin binding domain from *Bacillus circulans* is used as the fusion affinity-tag for *E. coli* contaminant proteins.

Where "matrix" is used, this is intended to refer to any of a porous or non-porous two dimensional surface coating of a surface such as a coating of surface of a reaction vessel or chip or three dimensional porous or non-porous structure such as a bead, column, or paper.

The host cell can be any bacterial cell such as *E. coli* or a eukaryotic cell that is capable of being transformed or transfected with a vector suitable for making a protein of interest.

Various vectors can be designed for use in homologous recombination such as for example, allele exchange vectors. A desirable feature of allele exchange vectors which recombine with the chromosome is the ability to select for those cells in which recombination has occurred. The examples of vectors provided here are not intended to be limiting and any person of ordinary skill in the art will appreciate that any selectable marker commonly in use will be effective. In the examples below, the pMAKCBD vector which contains a temperature-sensitive origin of replication, has a chloramphenicol selectable marker. These features allow for selection of cells where the vector is integrated in the chromosome when agar plates are incubated at the non-permissive temperature for plasmid replication. Alternatively, direct allele exchange may be performed by introduction of linear DNA into cells. Transformation of linear DNA is preferably linked to direct selection of cells with the desired phenotype. (Swingle B., et al., *Mol. Microbiol.* 75: 138-148 (2010)).

The examples provided demonstrate the proof of principle described here using a CBD-tag fused to the essential contaminating proteins. Any of the other affinity-tags described may be utilized for this purpose. The contaminating proteins naturally contain a plurality of histidines or other basic amino acids that are capable of binding to a nickel column along with His-tagged proteins of interest. For essential contaminating proteins, the activity of the protein must be preserved to maintain viability of the host cell in order to express the protein of interest.

Embodiments of the modified host cells described herein contain multiple contaminating essential proteins where some or all of the chromosomal genes encoding these proteins have been individually modified so as to be fused to a non-His-tag when expressed in the cell. In addition certain essential contaminating proteins may also be mutated such that the plurality of histidines (or basic amino acids) are replaced by a different amino acid such as alanine (GlmS)(see also Example 5).

All references cited herein are incorporated by reference including Robichon et al. Applied and Environmental Microbiology, 77, p 4634-4646 (2011) and provisional application 61/381,736 which is the priority document for the present application.

EXAMPLES

To assist in understanding the present embodiments of the invention strain genotypes and descriptions are given below:
Parent strain: ER3135=BL21(DE3) fhuA2
Thus ER3135=fhuA2 [lon] ompT gal (λ DE3) [dcm] ΔhsdS λ DE3 is defined as Δ sBamHIo LEcoRI-B int::(lacI::PlacUV5::T7 gene1) i21 Δnin5
Derivative 1: ER3200=ER3135 carrying the slyD-CBD allele
Derivative 2: ER3201=ER3135 carrying the slyD-CBD and can-CBD alleles
Derivative 3: ER3202=ER3135 carrying the slyD-CBD, can-CBD, and amA-CBD alleles
Derivative 4: ER3203=ER3135 carrying the slyD-CBD, can-CBD, arnA-CBD and aceE-CBD alleles
Derivative 5: ER3204=ER3135 carrying the slyD-CBD, can-CBD, arnA-CBD and glmS(6Ala) alleles aka (Nico21(DE3))
derivative 6: ER3205=ER3135 carrying the slyD-CBD, can-CBD, amA-CBD, aceE-CBD and glmS(6Ala) aka (Nico22 (DE3))

note: can is the carbonic anhydrase gene, also known as the yadF gene
arnA is also known as yfbG.

Example 1

Figure 1:
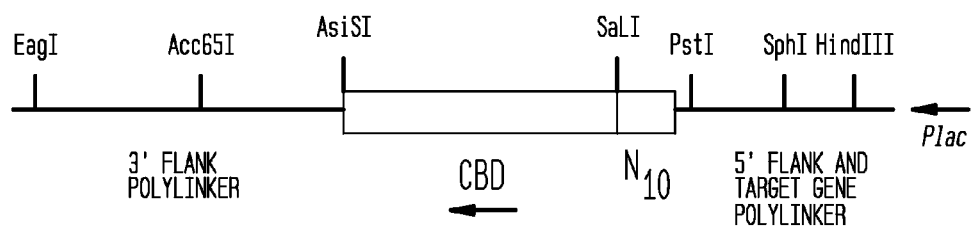
FIG. 1 shows pMAK-chitin binding domain (pMAKCBD) with a 3 prime polylinker sites and a 5 prime flank and target gene polylinker used for cloning of genomic DNA fragments for targeted allele exchange.

Construction of the pMAKslyD-CBD and Allele Exchange to Replace the Chromosomal slyD Gene with slyD-CBD The pMAK705 vector (Hamilton, et al., *Journal of Bacteriology:* 4617-4622 (1989)) was modified to create a vector for introducing the CBD affinity tag open reading frame (ORF) at the 3' end of chromosomal genes encoding contaminant proteins. CBD-ORF from vector pTYB1 (New England Biolabs, Inc., Ipswich, Mass.) was inserted into the polylinker region of pMAK705. A protein coding linker region was inserted upstream of the CBD-ORF. The linker region codes for the following nineteen amino acid sequence: LQASSS $(N)_{10}$LQS (SEQ ID NO: 4), where the first LQ codons correspond to a PstI restriction site and the last LQS codons contain a SalI restriction site. (See FIG. 1 for a polylinker map of the C-terminal CBD-tagging vector named pMAKCBD).

The allele exchange method described by Hamilton, et al. (1989) relies on homologous recombination. Efficient allele exchange occurs when the allele exchange vector contains at least 300 bp of homology to both the 5' and 3' regions flanking the target site on the bacterial host chromosome. These DNA segments of at least 300 bp are most easily isolated by PCR amplification from the target host chromosome and subsequently cloned into the allele exchange vector by restriction site ligation, ligase independent cloning (LIC), or uracil-specific excision reagent (USER) cloning (Sambrook, J., et al., *Molecular Cloning: A Laboratory Manual,* 2nd Ed., Cold Spring Harbor Laboratory Press, Cold Spring Harbor, N.Y. (1989); Aslanidis, C., et al., *Nucleic Acids Research* 18: 6069-6074 (1990); Haun, R. S., et al., *Biotechniques* 13: 515-518 (1992); and Bitinaite, J., et al., *Nucleic Acids Research* 35(6): 1992-2002 (207)). Alternatively, DNA fragments corresponding to target sites on the chromosome may be created by in vitro DNA synthesis techniques. We introduced useful restriction sites into the allele exchange vector to facilitate target gene cloning and 3' flanking DNA cloning (see FIG. 1). Genes encoding *E. coli* essential proteins that contaminate samples on a nickel column may be cloned into the unique HindIII, SphI and/or PstI(SbfI) sites in the pMAKCBD allele exchange vector. DNA corresponding to 3' gene flanking sequence may be cloned into the AsiSI, Acc65I and/or the EagI unique restriction sites to provide a 3' region of homologous sequence. FIG. 2 shows the nucleotide sequence of the pMAKCBD allele exchange vector.

pMAKslyD-CBD was constructed from pMAKCBD to replace the slyD allele in ER3135 with the slyD-CBD allele. The slyD gene of ER3135 was PCR-amplified with primers 4853 and 4854 and cloned into the HindIII and SbfI sites of pMAKCBD. In a second step, the 3' flanking DNA downstream from the slyD gene was PCR-amplified from the ER3135 using primers 4855 and 4856 and cloned into the AsiSI and EagI sites to create clone pMAKslyD-CBD.

TABLE 1

Primers and Primer Sequences for Construction of pMAKslyD-CBD

| Primer | Sequence† | Restriction Enzyme |
|---|---|---|
| 4853For | CCACC<u>AAAGCTT</u>GTTAAGTGCGGACATCAG (SEQ ID NO: 5) | HindIII |
| 4854Rev | GGTGGT<u>CCTGCAGG</u>TGGCAACCGCAACCGCCG (SEQ ID NO: 6) | SbfI |

TABLE 1-continued

Primers and Primer Sequences for Construction of pMAKslyD-CBD

| Primer | Sequence† | Restriction Enzyme |
|---|---|---|
| 4855For | CCACCA<u>GCGATCGC</u>ATACCGAAAAAGTGACAAAAAAGCG (SEQ ID NO: 7) | AsiSI |
| 4856Rev | GGTGGT<u>CGGCCGG</u>CAGCTTCAGCAGCAAAAGTGA (SEQ ID NO: 8) | EagI |

†Underlined nucleotides indicate the recognition sequence of the restriction enzyme named in the rightmost column.

SlyD was selected as the first contaminating essential protein to be tagged by the CBD-tag. pMAKslyD-CBD was transformed into ER3135 which is a T1-phage resistant version of BL21(DE3). We determined that selection of pMAK705-derived constructs in ER3135 was preferably undertaken using rich agar plates with chloramphenicol dosed at 4 ug/mL ("Rich-Cam4 plates"). The pMAKslyD-CBD construct was transformed into ER3135, and individual clones were grown in Rich-Cam4 liquid media until OD=0.5, and then approximately $2 \times 10^6$ colony forming units were plated on Rich-Cam4 agar. Plates were incubated at either 30° C. to allow plasmid replication or 42.5° C. to prevent plasmid replication. The ratio of colonies resulting from the two different plating temperatures was approximately 10,000/1. Thus, the chromosomal integration frequency was about 1 in $10^4$ cells. PCR analysis was carried out on individual colonies to confirm slyD locus integration by the pMAKslyD-CBD construct. slyD locus integration was confirmed by positive PCR amplification using a forward primer specific for the plasmid (s1233) and reverse primer 4060, annealing to the chromosomal DNA downstream of the slyD locus (and outside of the sequence cloned into pMAK-slyD-CBD). Positive integrants were inoculated into rich media with Cam concentration dosed at 10 ug/mL ("Rich-Cam10 media") and grown at 30° C. to enable re-activation of the plasmid origin of replication. The higher level of Cam (10 ug/mL) encourages growth of the strains where the pMAK construct becomes episomal. Thus, after three continuous outgrowths to saturation, the respective culture was populated with cells containing replicating plasmid. The plasmid allele was analyzed by PCR amplification using primers s1233 and s1224. Strains where allele exchange occurred were identified by the size of the PCR amplicon and additionally by resistance to MfeI digestion. The CBD-ORF contains a unique MfeI site that is useful for allele exchange analysis. The strains positive for allele exchange were cured of the pMAK vector carrying the WT slyD allele derived from the chromosome. pMAK vector curing was accomplished by coumermycin treatment (Chen, et al., *J. Biol. Chem.* 278: 23295-23300(2003)). The cured strain (ER3200) was genetically characterized by sequencing the slyD-CBD allele amplified by primers 4059 and 4060. PCR amplification with these two primers confirmed that the slyD-CBD allele was present at the correct position within the chromosome. The amplified ER3200 genomic DNA was sequenced to confirm the presence of an in-frame genetic fusion between the slyD gene and the CBD-ORF. Strain ER3200 exhibited the same growth rate in rich media when compared to parent strain ER3135.

TABLE 2

Primers and Primer Sequences for Allele Exchange to Create the slyD-CBD Derivative of ER3135

| Primer | Sequence |
|---|---|
| S1233For | AGCGGATAACAATTTCACACAGGA (SEQ ID NO: 9) |
| 4060Rev | GCACCCAGTGCATAAGCTGATTTCT (SEQ ID NO: 10) |
| S1224 | CGCCAGGG CCCAGTCACGAC (SEQ ID NO: 11) |
| 4059Forv | GCCTGTCAGGCGCAGGATTCA (SEQ ID NO: 12) |

Figure 3A:
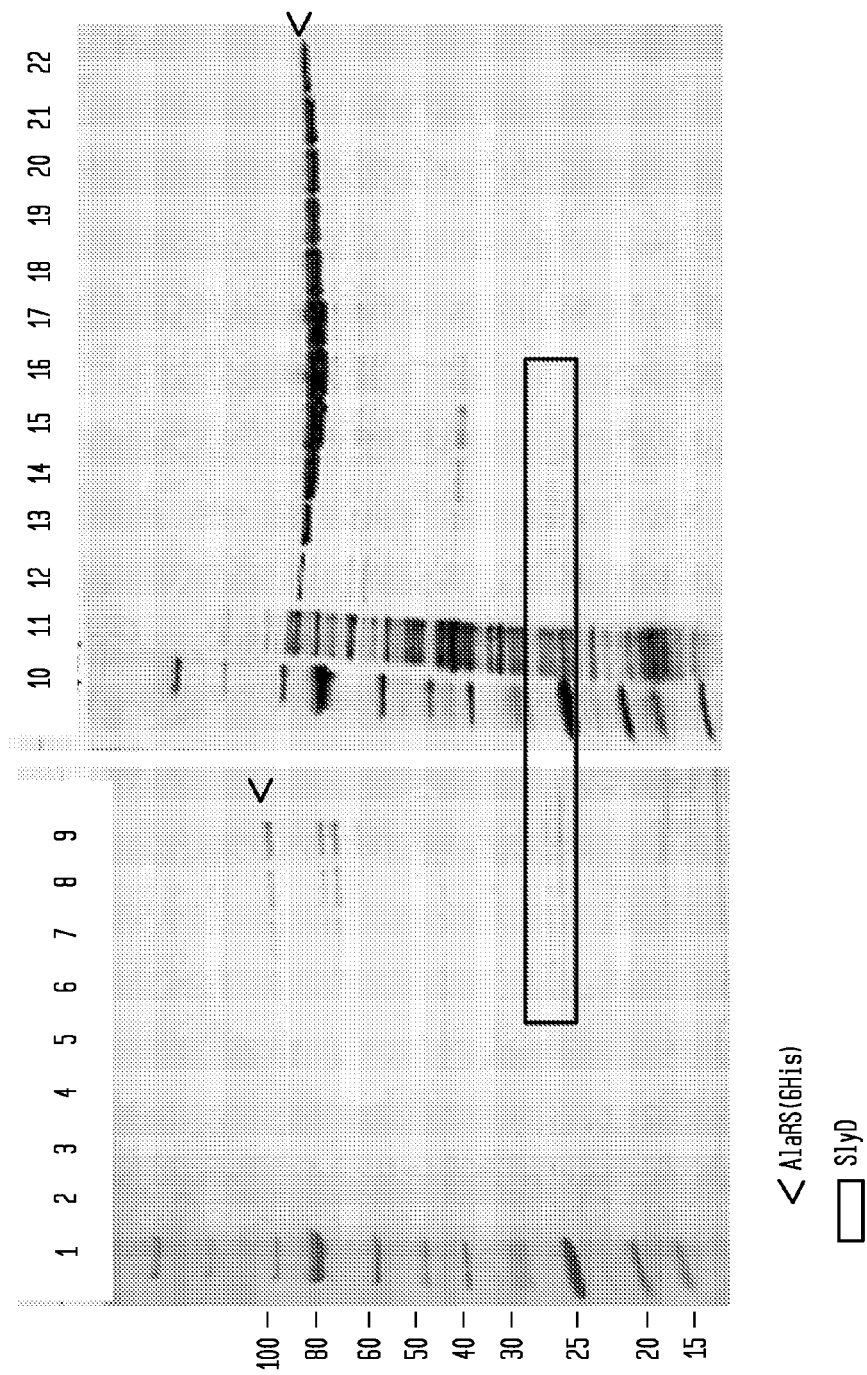
FIG. 3A shows the results of gel electrophoresis of samples obtained by column fractionation of cell lysates of ER3135 over-expressing a target protein; His6-tagged alanine tRNA synthetase (AlaRS(6His)). The column used here is an Ni-NTA column (HisTrap™ column; GE Healthcare, Waukesha, Wis.).

FIG. 3A demonstrates the problem of wild type SlyD co-eluting from Ni-NTA resin with the his-tagged protein of interest (also referred to as a target protein) over-expressed in parent strain ER3135. FIG. 3B shows co-elution of SlyD-CBD from Ni-NTA resin with the target protein after over-expression in the slyD-CBD derivative strain ER3200. Note that SlyD-CBD protein exhibits a much slower migration rate in SDS-PAGE when tagged with the 7 kDa CBD-tag. FIG. 3C confirms that the most of the Ni-NTA elution fractions shown in FIG. 3B are contaminated with the SlyD-CBD fusion protein (prior to chitin affinity chromatography).

Example 2

Construction of pMAKcan-CBD and Allele Exchange to Tag the Chromosomal can Carbonic Anhydrase Gene A second contaminating essential protein chosen for tagging was the can gene product carbonic anhydrase. The 3' flanking DNA downstream of the can gene (formerly yadF) was PCR-amplified from ER3135 genomic DNA using primers 4839 and 4840 and cloned into the AsiSI and EagI sites of pMAKCBD. The can gene was PCR-amplified from ER3135 genomic DNA using primers 4841 and 4842 and cloned into the HindIII and SacI sites. The resulting construct pMAKcan-CBD was confirmed by DNA sequencing and then transformed into ER3135. The allele exchange procedure was carried out in the same manner described in Example 1, except that chromosomal integration analysis and can locus amplification were accomplished using primers 4841 and 2187.

The can-CBD derivative of ER3135 exhibited the same growth rate in rich media as the parent strain. Thus, we proceeded to add the can-CBD allele to strain ER3200 (slyD-CBD strain) by allele exchange to create the double CBD-tagged derivative ER3201, which also exhibited the same growth rate in rich media when compared to parent strain ER3135.

TABLE 3

Primers and Primer Sequences for Construction of pMAKcan-CBD and Allele Exchange

| Primer | Sequence | Restriction Enzyme |
|---|---|---|
| 4839For | ACCACCGCGATCGCAAATGCCATGCCGGATGCAACACATCC (SEQ ID NO: 13) | AsiSI |
| 4840Rev | ACCACCCGGCCGCATATGGTTAGAGATATGAAACATAC (SEQ ID NO: 14) | EagI |
| 4841For | ACCACCAAGCTTCGAGATCGTAACCAAATACGCTG (SEQ ID NO: 15) | HindIII |
| 4842Rev | ACCACCGAGCTCGATTTGTGGTTGGCGTGTTTCAGCTTGAG (SEQ ID NO: 16) | SacI |
| 2187Rev | CGAGTAATCGTCGCGAGCCTGTATTG (SEQ ID NO: 17) | |

†Underlined nucleotides indicate the recognition sequence of the restriction enzyme named in the rightmost column.

Example 3

Construction of pMAKarnA-CBD-arnD and Allele Exchange to Tag the Chromosomal arnA Gene at the 3'End The ArnA protein was selected as the third contaminating essential protein for CBD-tagging. The amA gene resides within an operon where the amA stop codon overlaps the downstream arnD gene start codon (ATGA). To maintain this native genetic context at the arnA/arnD junction, we designed the arnA-CBD-arnD allele to encode the last 4 codons of amA after the CBD-ORF so that the native arnA/arnD junction would be maintained. This engineered allele expresses an ArnA-CBD fusion protein with the DKPS amino acid sequence repeated before and after the C-terminal CBD-tag. The pMAKarnA-CBD-arnD construct was created as follows. First, the arnD gene was PCR-amplified from ER3135 genomic DNA using primers 9990 and 0001 (see Table 4). Next, the pMAKCBD vector was PCR-amplified using primers 0003 and 9991 to create a blunt ended DNA that ends with the last codon of the CBD-ORF. Ligation of these two fragments creates a genetic fusion coding for CBD-DKPSArnD. Finally, the amA gene was PCR-amplified from ER3135 genomic DNA using primers 0000 and 0002 and cloned into the HindIII and PstI sites to create the final allele exchange construct pMAKarnA-CBD-arnD.

The arnA-CBD-arnD allele was inserted at the arnA-arnD locus of ER3135 using the allele exchange method as described in Examples 1 and 2. Chromosomal integration analysis and arnA-arnD locus amplification was accomplished using primers 5032 and 5031. The arnA-CBD-arnD derivative of ER3135 exhibited the same growth rate in rich media when compared to parent strain ER3135. Thus, the arnA-CBD-arnD allele was also added to strain ER3201 to create the triple CBD-tagged strain ER3202.

TABLE 4

Primers and Primer Sequences for Construction of pMAKarnA-CBD-arnD and Allele Exchange

| Primer | Sequence†‡ | Restriction Enzyme |
|---|---|---|
| 9990For | P-GATAAACCATCATGACCAAAGTAGG (SEQ ID NO: 18) | |
| 0001Rev | CAGGTGGGTACCGTCACCGGAATTTGCG (SEQ ID NO: 19) | Acc65I |
| 0003 | GATATTGCTGGGTACCGAGCTCGAA (SEQ ID NO: 20) | Acc65I |
| 9991 | P-TTGAAGCTGCCACAAGGCAGGAACG (SEQ ID NO: 21) | |
| 0000For | CGGCATAAGCTTACTCGGTGAATATATCGG (SEQ ID NO: 22) | HindIII |
| 0002Rev | P-AGCCTGCAGGGAAGGTTTATCCGTAAGATCAACGGTGCG (SEQ ID NO: 23) | |
| 5032For | GATGTACGACCTGGTGACCTGC (SEQ ID NO: 24) | |
| 5031Rev | GGATGCGGTTGAGTAACCAACC (SEQ ID NO: 25) | |

†Underlined nucleotides indicate the recognition sequence of the restriction enzyme named in the rightmost column.
‡"P" indicates the position of phosphorylation.

Example 4

Construction of pMAKaceE-CBD and Allele Exchange to Tag the Chromosomal aceE Gene at the 3'End The AceE protein was selected as the fourth contaminating essential protein for CBD-tagging. The aceE gene codes for the E1 subunit of the pyruvate dehydrogenase mufti-subunit complex. The downstream chromosomal gene is aceF, which codes for the E2 subunit of the pyruvate dehydrogenase complex. Together with the dihydrolipoyl dehydrogenase subunit (E3), this key metabolic enzyme is composed of E1:E2:E3 at a ratio of 24:24:12 subunits per complex in *E. coli* (Lehninger et al. *"Principles of Biochemistry"* $2^{nd}$ edition, 1993 by Worth Publishers). Thus, the expression level of each subunit is important to the viability of the cell.

The pMAKaceE'-CBD-aceF allele exchange clone maintained the native 14 nucleotide spacing between the aceE and aceF genes: TAAGAGGTAAAAGAATAATG (SEQ ID NO: 26). The aceE' designation indicates that the aceE gene is truncated at the 5' end. Thus, integrants were not isolated in the first step of the allele exchange method if the aceE-CBD allele was not tolerated. pMAKaceE'-CBD-aceF was constructed as follows: First, the full-length aceE gene was cloned using primers 4845 and 4846 (see Table 5). Then, the 5' end of aceE was deleted by SphI-BsiWI digestion, followed by a blunting reaction with Klenow fragment and ligation to reclose the plasmid. Next, the full-length aceF gene was PCR-amplified from ER3135 using primers 0077 and 0076 and cloned into the deltaSphI-BsiWI clone. The vector fragment was prepared by PCR-amplification using 0079 and 0078 and subsequent digestion with EagI.

pMAKaceE'-CBD-aceF allele exchange construct was transformed into the triple CBD-tagged strain ER3202 to create the quadruple CBD-tagged strain ER3203. Primers 4845 (upstream forward) and 0078 (CBD-tag reverse) were used to confirm proper integration at the aceE locus. Primers 4845 and 0076 were used to PCR-amplify the aceE locus for sequence characterization. The amplicon was digested with MfeI to rapidly identify the strains encoding aceE-CBD at the aceE locus as the WT aceE gene lacks this site and the CBD-ORF contains a single MfeI site.

Strain ER3203 exhibited a reduced growth rate in rich media when compared to parent strain ER3135. However, the same cell density was obtained after overnight shaking (225 rpm at 37° C. in 2 L flasks). Under high-density cultivation conditions, ER3203 achieved a saturation density of OD600=31.6, whereas ER3135 achieved a saturation density of OD600=91.3 when both strains were induced with 1 mM IPTG to over-express Alanyl tRNA-synthetase(6His) from a plasmid. In the same experiment, the triple CBD-tagged strain ER3202 achieved a saturation density of OD=100.1 and the 6His expression level was comparable to the expression level observed in ER3135.

primers HindIII-g/mS For and g/mS-SacI Rev (see Table 6). This PCR product corresponding to the glmS gene with 200 bp 5' flanking sequence and no 3' flanking sequence was cloned into the HindIII and SacI sites of pMAK705.

pMAK-glmS(2Ala) was generated by PCR amplification of the plasmid pMAK-glmS with the reverse primer 3 (His62Ala) and forward primer 4 (His65Ala) and followed by ligation to circularize the linear PCR product (Phusion® Site-Directed Mutagenesis Kit, New England Biolabs, Inc., Ipswich, Mass.). The glmS(2Ala) gene has the sequence GCTCCTCTGGCT (SEQ ID NO: 33) modified from the WT sequence (CATCCTCTGCAT) (SEQ ID NO: 34) so that the four mutated nucleic acids resulted in alanine codons at positions 62 and 65 of the glmS ORF.

pMAK-glmS(4Ala) was generated by PCR amplification of the plasmid pMAK-glmS(2Ala) with the reverse primer 5 (His432Ala) and forward primer 6 (His436Ala) followed by the ligation to circularize the linear PCR product. The glmS (4Ala) has the sequence GCTGACATTGTGGC (SEQ ID NO: 35) modified from the glmS(2Ala) sequence (CATGACATTGTGCAT) (SEQ ID NO: 36) so that the four mutated nucleic acids resulted in additional alanine codons at positions 432 and 436 of the glmS ORF.

pMAK-glmS(6Ala) was generated by 2 PCR amplifications. First, the pMAK-glmS(4Ala) template was amplified with the reverse primer 7 containing two mutated bases resulting in a DNA encoding (His466Ala) in the GlmS and the forward primer 8 (His467Ala) and followed by the ligation of the linear PCR product to generate the plasmid pMAK-glmS(5Ala) (His62Ala, His65Ala, His432Ala, His436Ala, His466Ala). Second, the pMAK-glmS(5Ala) template was amplified with the reverse primer 9 (His466Ala) and the forward primer 10 (His467Ala) followed by ligation of the linear PCR product to generate the plasmid pMAK-glmS(6Ala). The glmS(6Ala) has the sequence AAAGCT

TABLE 5

Primers and Primer Sequences for Tagging the 3' End of the aceE Gene with the CBD-ORF

| Primer | Sequence†‡ | Restriction Enzyme |
|---|---|---|
| 4845For | ACCACCGCATGCGAATTGCTCTATTCGCGTCGCGAGATG (SEQ ID NO: 27) | SphI |
| 4846Rev | ACCACCGAGCTCGACGCCAGACGCGGGTTAACTTTATCTGC (SEQ ID NO: 28) | SacI |
| 0077For | P-GAGGTAAAAGAATAATGGCTATCG (SEQ ID NO: 29) | |
| 0076Rev | CAAACGGCGGCCGCTTTGTCTATTCGCTA (SEQ ID NO: 30) | NotI |
| 0079For | CAGCTCCGGCCGACGCGCTGGGCT (SEQ ID NO: 31) | EagI |
| 0078Rev | P-TTATTGAAGCTGCCACAAGGCAGG (SEQ ID NO: 32) | |

†Underlined nucleotides indicate the recognition sequence of the restriction enzyme named in the rightmost column.
‡"P" indicates the position of phosphorylation.

Example 5

Construction and Evaluation of GlmS Mutants with Either Two or Six Surface Histidines Replaced by Alanines The chromosomal glmS gene was mutated to replace histidine codons with alanine codons so that the respective strain would express a GlmS protein with reduced affinity for IMAC resins. FIG. 5 shows positions of histidine codons within the glmS gene, which were mutated to alanine in the mutants described below.

The pMAK-glmS clone was generated by PCR amplification of the glmS gene from ER3135 genomic DNA with the GCCGCG (SEQ ID NO: 37) modified from the glmS(4Ala) sequence (AAACATCACGCG) (SEQ ID NO: 38) so that the four mutated nucleic acids resulted in additional alanine codons at positions 466 and 467 of the glmS ORF.

FIG. 6 shows results from over-expressing the WT GlmS protein, the GlmS(2Ala) protein and the GlmS(6Ala) protein from the pMAK vector (lac promoter) in ER3135. In each case, cell lysates were prepared and subjected to ÄKTA™ HisTrap™ chromatography (GE Healthcare, Waukesha, Wis.). The results show that the GlmS(6Ala) does not bind to the HisTrap™ resin whereas the GlmS wild type protein and the GlmS(2Ala) do bind to the resin in the presence of 20 mM imidazole.

TABLE 6

Primers and Primer Sequences for Construction and Evaluation of GlmS Mutants

| Primer | Sequence* |
|---|---|
| HindIII-glmS For | GGAGGAAAGCTTGACTCAGAAAGAAGGCTGG (SEQ ID NO: 39) |
| glmS-SacI Rev | CCACCAGAGCTCTTATTACTCAACCGTAACCGATTTTGCC (SEQ ID NO: 40) |
| His62-Ala Rev | GGAGCTTCTTCCGCTGCCTGAGCC (SEQ ID NO: 41) |
| His65Ala For | TCTGGCTGGCGGCACCGGTATTGCTCAT (SEQ ID NO: 42) |
| His432Ala Rev | ATGTCAGCTTCAATGGAGGCATCCAGACCTT (SEQ ID NO: 43) |
| His436Ala For | TGTGGCTGGTCTGCAGGCGTTGCCGAGCCGTAT (SEQ ID NO: 44) |
| His466Ala Rev | AGCTTTGTCAGAGAAATCTTC (SEQ ID NO: 45) |
| glmS467 For | CACGCGCTGTTCCTGGGCCGT (SEQ ID NO: 46) |
| glmS466 REV | ATGTTTGTCAGAGAAATCTTC (SEQ ID NO: 47) |
| His467Ala For | GCCGCGCTGTTCCTGGGCCGTGGCGATCAG (SEQ ID NO: 48) |

*Bold and underlined nucleotides indicate mutations relative to WT glmS sequence.

Example 6

Allele Exchange to Introduce the glmS(6Ala) Mutant Gene pMAK-glmS(6Ala) construct was transformed into strains ER3202 and ER3203 and the allele exchange method was used to replace the chromosomal WT glmS gene with the glmS(6Ala) gene. The protein expression host derived from ER3202 was named NiCo21(DE3) and the host derived from ER3203 was named NiCo22(DE3).

Example 7

Mass Spectrometry Analysis of *E. coli* Ni-NTA Binding Proteins from: ER3135, Nico21(DE3) and Nico22(DE3)

Mass spectrometry analysis of *E. coli* proteins which bound to a Ni-NTA column (Qiagen, Germantown, Md.) from: ER3135, Nico21(DE3) and Nico22(DE3). Each strain was grown to saturation at 37° C. in luria broth (LB) plus 0.1% glucose. Cell pellets were resuspended in buffer A [20 mM sodium phosphate (pH 7.4), 0.5M NaCl, 20 mM imidazole] and sonicated to prepare a cell lysate. The clarified lysate was loaded onto a 1 mL HisTrap™ column. The column was washed with 90 column volumes of buffer A (20 mM imidazole). Then the high affinity Ni-NTA binding proteins were eluted with buffer A containing 400 mM imidazole. The eluted proteins were analyzed by mass spectrometry. Zero GlmS peptides were detected in the samples originating from Nico21(DE3) and Nico22(DE3) in contrast to the parent strain where GlmS was the primary Ni-NTA binding protein.

Example 8

Overexpression of Target Protein Alanyl tRNA-Synthetase in ER3135, Nico21(DE3) and Nico22(DE3)

The *E. coli* protein contaminant profile was evaluated when His-tagged Alanyl tRNA synthetase was over-expressed from pQE30 (Qiagen, Germantown, Md.) in three strains of interest: ER3135=BL21(DE3) fhuA versus Nico21(DE3) versus Nico22(DE3). Note that each strain also carried the miniF-lacIq plasmid isolated from T7 Express I$^q$ (New England Biolabs, Inc., Ipswich, Mass.). Cell lysates resulting from 500 mL of IPTG-induced cells were loaded, washed and eluted from a 5 mL HisTrap™ column according to manufacturer's recommendations. The imidazole elution fractions enriched in 6His were pooled (see lanes P in FIG. 7). The Ni-NTA pools (P) were passed through a chitin column. The proteins flowing through the chitin column are shown in lanes FT in FIG. 7. Finally, lanes labeled B were the result of boiling the chitin resin in the presence of SDS to strip the resin of CBD-tagged proteins. As expected, very little protein is present in FIG. 7 lane B of ER3135 since this is the parent strain lacking CBD-tagged proteins. In contrast, lanes B corresponding to Nico21(DE3) and Nico22(DE3) are enriched with CBD-tagged proteins that have been removed from the target protein (as indicated in FIG. 7). A black triangle indicates the 67 kDa GlmS protein in lanes P and FT of ER3135, whereas the GlmS protein is absent in all lanes corresponding to Nico21(DE3) and Nico22(DE3).

What is claimed is:

1. A composition, comprising: a variant host cell derived from a parent host cell, the parent host cell characterized by a genome encoding a plurality of essential host proteins containing a plurality of histidines or basic amino acids residues such that when the cell is lysed, the essential proteins are capable of binding to a metal chelating matrix; wherein the variant host cell that is viable and differs from the parent host cell in that in the variant host cell:
   (a) at least one of the plurality of essential host proteins is additionally fused to an affinity binding tag encoded by the genome, the fusion proteins being capable of binding to a non-metal affinity matrix; or
   (b) at least one of the plurality of essential host proteins is mutated such that at least two of the plurality of histidines or basic amino acid residues are replaced with non-histidine residues so that the mutated essential protein is no longer able to bind the metal chelating matrix;
the variant host cell being capable of being transformed to express a recombinant target protein.

2. A composition according to claim 1, wherein one or more of the essential host proteins fused to an affinity binding tag is selected from the group consisting of: SlyD, carbonic anhydrase (can), ArnA, ArnD AceE, AceF and GlmS.

3. A composition according to claim 1, wherein the variant host cell further comprising a non-host DNA encoding a protein of interest.

4. A composition according to claim 1, wherein at least two histidines in the at least one of a plurality of essential host protein are changed to alanines.

5. A composition according to claim 1, wherein the affinity binding tag is selected from an immunoaffinity tag, a peptide tag selected from hemagglutinin, c-myc, T7, Glu-Glu, GST-tag, ZZ, GB1, MCP, and ACP, a streptavidin binding tag or a chitin binding domain tag.

6. A composition according to claim 1, wherein the parent host cell is a prokaryotic host cell.

7. A composition according to claim 6, wherein the bacterial cell is an *E. coli*.

8. A method of isolating a recombinant target protein from a cell lysate, comprising:
   (a) lysing variant host cells according to claim 1, wherein the variant host cells are transformed with DNA encoding a target protein fused to a histidine-tag;
   (b) subjecting the lysed host cells to a metal chelating matrix and a non-metal affinity binding matrix; and
   (c) isolating the recombinant protein from the cell lysate.

9. A method according to claim 8, wherein the metal chelating matrix and the non-metal affinity binding matrix are contained in the same reaction vessel.

10. A method according to claim 8, wherein the metal chelating matrix and the non-metal affinity binding matrix are contained in different reaction vessels.

11. A method of isolating a recombinant protein from a cell lysate, comprising:
   (a) lysing host cells that express: a recombinant protein fused to a His-tag; a plurality of essential proteins containing histidine residues or basic amino acids, wherein the one or more of the essential proteins are capable of binding to a metal chelating matrix and wherein the one or more essential proteins are additionally fused to an affinity binding tag; and optionally one or more essential proteins in which histidine or basic amino acid residues have been mutated so that the one or more essential proteins no longer bind to a metal chelating matrix;
   (b) subjecting the lysed host cells to at least one of a metal chelating matrix and a non-metal binding matrix; and
   (c) isolating the recombinant protein from the cell lysate.

12. A composition according to claim 1, wherein the parent host cell is a eukaryotic host cell.

* * * * *